US006450390B2

(12) United States Patent
Heck et al.

(10) Patent No.: US 6,450,390 B2
(45) Date of Patent: Sep. 17, 2002

(54) SURGICAL ANASTOMOSIS APPARATUS AND METHOD THEREOF

(75) Inventors: Christopher F. Heck, Plymouth, MN (US); Lee R. Bolduc, Mountain View, CA (US)

(73) Assignee: Hearport, Inc., Redwood City, CA (US)

(*) Notice: Subject to any disclaimer, the term of this patent is extended or adjusted under 35 U.S.C. 154(b) by 0 days.

(21) Appl. No.: 09/756,426

(22) Filed: Jan. 8, 2001

Related U.S. Application Data

(63) Continuation of application No. 09/488,140, filed on Jan. 20, 2000, now Pat. No. 6,176,413, which is a division of application No. 09/267,247, filed on Mar. 12, 1999, now Pat. No. 6,253,984, which is a division of application No. 08/979,831, filed on Nov. 20, 1997, now Pat. No. 5,881,943, which is a continuation of application No. 08/759,110, filed on Dec. 2, 1996, now abandoned, which is a continuation-in-part of application No. 08/550,285, filed on Oct. 31, 1995, now Pat. No. 5,709,335, which is a continuation of application No. 08/261,167, filed on Jun. 17, 1994, now abandoned.

(51) Int. Cl.[7] ............................................. A61B 17/068
(52) U.S. Cl. .................... 227/176.1; 227/19; 227/179.1; 606/219
(58) Field of Search ................................ 227/19, 175.1, 227/176.1, 178.1, 179.1; 606/219, 194

(56) References Cited

U.S. PATENT DOCUMENTS

| 1,251,258 A | 12/1917 | Magill |
| 1,756,670 A | 4/1930 | Treat |
| 1,918,890 A | 7/1933 | Bacon |
| 1,967,056 A | 7/1934 | Horton |
| 2,434,030 A | 1/1948 | Yeomans |

(List continued on next page.)

FOREIGN PATENT DOCUMENTS

| DE | 1250709 | 7/1961 |
| DE | 3115835 | 10/1982 |

(List continued on next page.)

OTHER PUBLICATIONS

Androsov, "New Method of Surgical Treatment of Blood Vessel Lesions," *Arch. Surg*, 1956;73:262–265.

(List continued on next page.)

*Primary Examiner*—Scott A. Smith

(57) ABSTRACT

The present invention provides a method and end-to-side surgical anastomosis apparatus for stapling an end of a tubular tissue structure to a side of a luminal structure including an elongated housing defining a central bore extending longitudinally therethrough. The elongated housing further includes an eversion support surface extending circumferentially about the bore opening adjacent the distal end which is configured to retain and support an everted end of the received tissue structure thereon to face an intimal surface of the tissue structure in an outward direction. The anastomosis apparatus further includes an anvil having a fastener engaging surface, and a compression device having a shoulder portion formed for selectively compressing the everted end of the tissue structure and a surface of the luminal structure together against the fastener engaging surface. The compression device is further formed to deform the fasteners into contact with the everted end of the tubular tissue structure and the luminal structure to create an anastomotic bond between the tubular tissue structure and the luminal structure. At least one driver pin, is preferably provided moveable relative to the compression device for ejecting the plurality of fasteners through the everted end of the tubular tissue structure and the luminal structure to engage the fastener engaging surface. This engagement deforms the fastener and creates an anastomotic bond between the tubular tissue structure and the luminal structure.

5 Claims, 20 Drawing Sheets

U.S. PATENT DOCUMENTS

| | | |
|---|---|---|
| 2,638,901 A | 5/1953 | Sugarbaker |
| 2,707,783 A | 5/1955 | Sullivan |
| 3,040,748 A | 6/1962 | Klein et al. |
| 3,080,564 A | 3/1963 | Strekopitov et al. |
| 3,193,165 A | 7/1965 | Akhalaya et al. |
| 3,217,557 A | 11/1965 | Martinot |
| 3,252,643 A | 5/1966 | Strekopytov et al. |
| 3,254,650 A | 6/1966 | Collito |
| 3,254,651 A | 6/1966 | Collito |
| 3,269,630 A | 8/1966 | Fleicher |
| 3,276,710 A | 10/1966 | Zernov et al. |
| 3,388,847 A | 6/1968 | Kasulin et al. |
| 3,452,615 A | 7/1969 | Gregory |
| 3,494,533 A | 2/1970 | Green et al. |
| 3,519,187 A | 7/1970 | Kapitanov |
| 3,552,626 A | 1/1971 | Astafiev et al. |
| 3,570,497 A | 3/1971 | Lemole |
| 3,589,589 A | 6/1971 | Akopov |
| 3,593,903 A | 7/1971 | Astafiev et al. |
| 3,638,652 A | 2/1972 | Kelley |
| 3,692,224 A | 9/1972 | Astafiev et al. |
| 3,774,615 A | 11/1973 | Lim et al. |
| 3,805,793 A | 4/1974 | Wright |
| 3,915,399 A | 10/1975 | Kron et al. |
| 4,009,841 A | 3/1977 | Matalia |
| 4,076,162 A | 2/1978 | Kapitanov et al. |
| 4,166,466 A | 9/1979 | Jarviik |
| 4,304,236 A | 12/1981 | Conta et al. |
| 4,319,576 A | 3/1982 | Rothfuss |
| 4,325,376 A | 4/1982 | Klieman et al. |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,466,436 A | 8/1984 | Lee |
| 4,505,414 A | 3/1985 | Filipi |
| 4,523,592 A | 6/1985 | Daniel |
| 4,553,542 A | 11/1985 | Schenck et al. |
| 4,573,468 A | 3/1986 | Conta et al. |
| 4,576,167 A | 3/1986 | Noiles |
| 4,586,503 A | 5/1986 | Kirsch et al. |
| 4,592,354 A | 6/1986 | Rothfuss |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,646,745 A | 3/1987 | Noiles |
| 4,657,019 A | 4/1987 | Walsh et al. |
| 4,665,906 A | 5/1987 | Jervis |
| 4,700,703 A | 10/1987 | Resnick et al. |
| 4,703,887 A | 11/1987 | Clanton et al. |
| 4,747,407 A | 5/1988 | Liu et al. |
| 4,763,851 A | 8/1988 | Flament |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,936,942 A | 6/1990 | Sollinger et al. |
| 4,957,499 A | 9/1990 | Lapstove et al. |
| 5,119,983 A | 6/1992 | Green et al. |
| 5,197,649 A | 3/1993 | Bessler et al. |
| 5,234,447 A | 8/1993 | Kaster et al. |
| 5,242,457 A | 9/1993 | Akopov et al. |
| 5,271,543 A | 12/1993 | Grant et al. |
| 5,292,053 A | 3/1994 | Bilotti et al. |
| 5,324,447 A | 6/1994 | Lam et al. |
| 5,330,503 A | 7/1994 | Yoon |
| 5,333,773 A | 8/1994 | Main et al. |
| 5,336,233 A | 8/1994 | Chen |
| 5,348,259 A | 9/1994 | Blanco et al. |
| 5,366,462 A | 11/1994 | Kaster et al. |
| 5,395,030 A | 3/1995 | Kuramoto et al. |
| 5,403,333 A | 4/1995 | Kaster et al. |
| 5,478,354 A | 12/1995 | Tovey et al. |
| 5,522,834 A | 6/1996 | Fonger et al. |
| 5,549,619 A | 8/1996 | Peters et al. |
| 5,554,162 A | 9/1996 | DeLange |
| 5,588,479 A | 12/1996 | Schmut et al. |
| 5,620,452 A | 4/1997 | Yoon |
| 5,669,918 A | 9/1997 | Balazs et al. |
| 6,176,413 B1 * | 1/2001 | Heck et al. ............... 227/176.1 |

FOREIGN PATENT DOCUMENTS

| | | |
|---|---|---|
| DE | 4222251 | 1/1994 |
| EP | 0137685 | 4/1985 |
| EP | 0 419 660 A1 | 1/1990 |
| EP | 0 384 647 A1 | 8/1990 |
| FI | 88386 | 12/1988 |
| FR | 1518083 | 3/1968 |
| GB | 935490 | 9/1959 |
| GB | 2038692 | 7/1980 |
| GB | 2108418 | 5/1986 |
| NL | 7711347 | 4/1979 |
| SU | 995765 | 2/1983 |
| SU | 1097301 | 6/1984 |

OTHER PUBLICATIONS

Inokuchi, "Stapling Device for End–to–side Anastomosis of Blood Vessles," *Arch Surg*, 1961;82:27–31.

Vogelfanger et al., "A Concept of Automation in Vascular Surgery: A Preliminary Report on a Mechanical Instrument for Arterial Anastomosis," *Can J Surg*, 1958;58:262–265.

Holt et al., "A New Technique for End–to–end Anastomosis of Small Arteries," Surg Forum, 1960;11:242.

Rohman et al., Chapter IX—Cardiovascular Technique, "Double Coronary Artery–internal Mammary Artery Anastomoses, Tantalum Ring Technique," *Surg Forum*, 1960:11:236–243.

Goetz et al., "Internal Mammary–coronary Artery Anastomosis: A Nonsuture Method Employing Tantalum Rings", *J Thorac Card Surg*, 1961:41(3):378–386.

Inokuchi, "A New Type of Vessel–suturing Apparatus," *AMA Arch Surg*, 1958;77:954–957.

Nakayama et al., "A Simple New Apparatus for Small Vessel Anastomosis (free autograft of the sigmoid included)," *Surgery*, 1962;52(6):918–931.

Cooper et al., "Development of the Surgical Stapler with Emphasis on Vascular Anastomosis," *NY Acad. Sci*, 1963;25:365–377.

Miller, "The Russian Stapling Device," *NY Acad Sci*, 1963;25:378–381.

Narter et al., "An Experimental Method for Nonsuture Anastomosis of the Aorta," *Surg Gyne & Obs*, 1964;632–361.

Gottlob et al., "Anastomoses of Small Arteries and Veins by Means of Bushings and Adhesive," *J Card Surg*, 1968;9:337–341.

Guyton et al., "A Mechanical Device for Sutureless Aorta—Saphenous Vein Anastomosis," *Ann Thorac Surg*, 1979;28:342–345.

Gentili et al., "A Technique for Rapid Non–suture Vascular Anastomosis," *Can J Neuro Sci*, 1987;14(1):92–95.

Olearchyk, "Vasilii I. Kolesov—A Pioneer of Coronay Revascularization by Internal Mammary–coronary Artery Grafting," *J Thorac Surg*, 1988;96(1);13–18.

Ragnarsson et al., "Microvenous End–to–Side Anastmosis: An experimental Study Comparing the UNILINK System and Sutures," *J Reconstruct Microsurg*, 1989;5(3):217–224.

Ragnarsson et al,. "Arterial End–to–side Anastomosis with the UNILINK System," *Ann Plastic Surg*, 1989;22(3):405–415.

Li et al., "End–to–side–anastomosis in the Dog Using the 3M Precise Microvascular Anastomotic System: A Comparative Study," *J Reconstruct Microsurg*, 1991:7(4):345–350.

Kirsch et al., "A New Method for Microvascular Anastomosis: Report of Experimental and Clinical Research," *American Surgeon*, 1992;58:722–727.

Lanzetta et al., "Long–term Results of 1 Millimeter Arterial Anastomosis Using the 3M Precise Microvascular Anastomotic System," *Microsurgery*, 1992:13:313–320.

Berggren et al., "Clinical Experience with UNILINK 3M Precise Microvascular Anastomotic Device," *Scand J Plast Reconstr Hand Surg*, 1993;27:35–39.

Gentili et al., "A Technique for Rapid Non–suture Vascular Anastomosis," Can. J Neuro Sci., 10987;14(1):92–95.

Holt et al., "A New Method for Microvascular Anastomosis: Report of Experimental and Clinical Research," The American Surgeon, 1992;58(12):722–727.

Kirsch et al., "A New Technique for End–to–end Anastomosis of Small Arteries" Surgical Forum, 1960;11:242–243.

\* cited by examiner

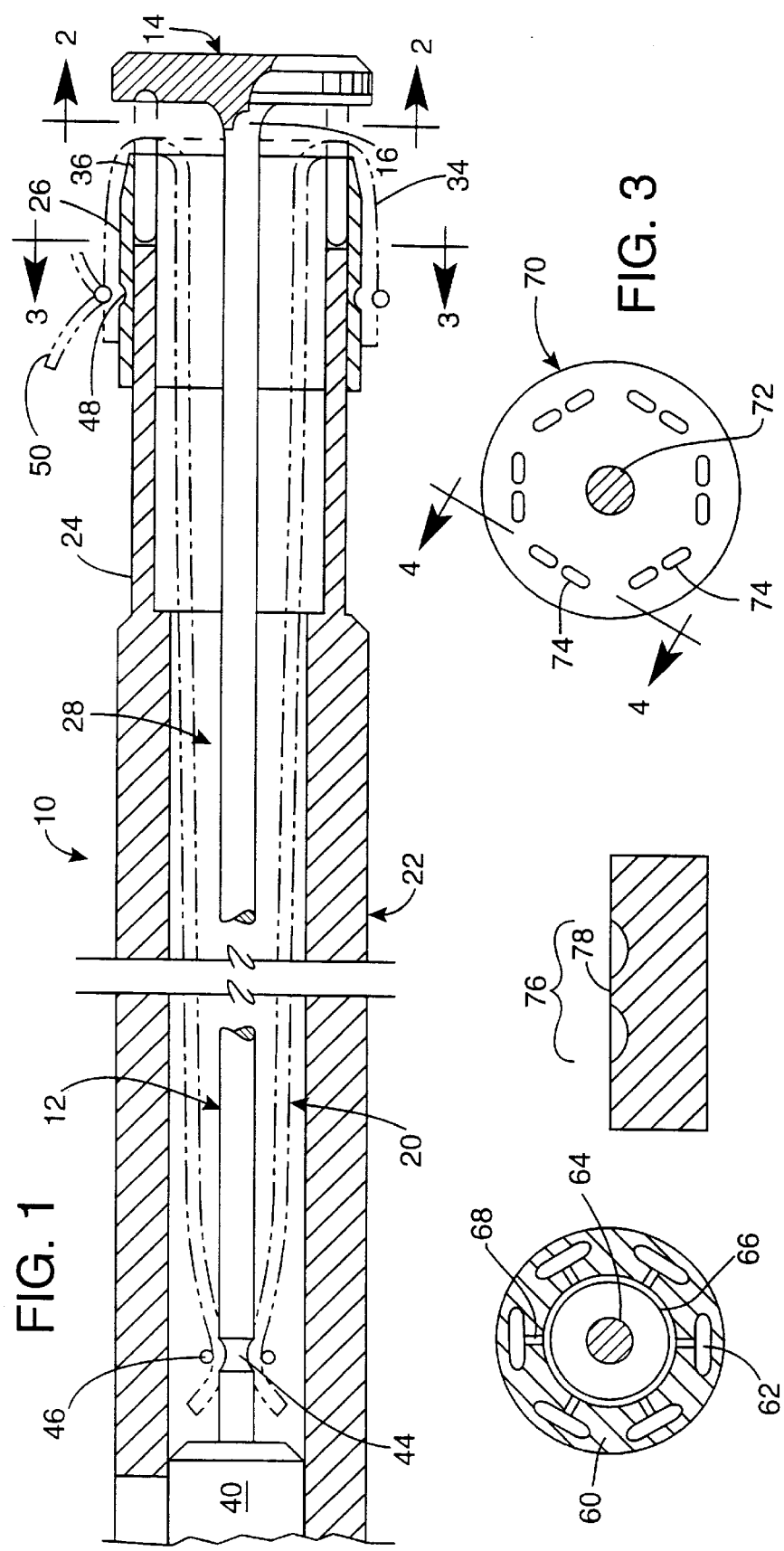

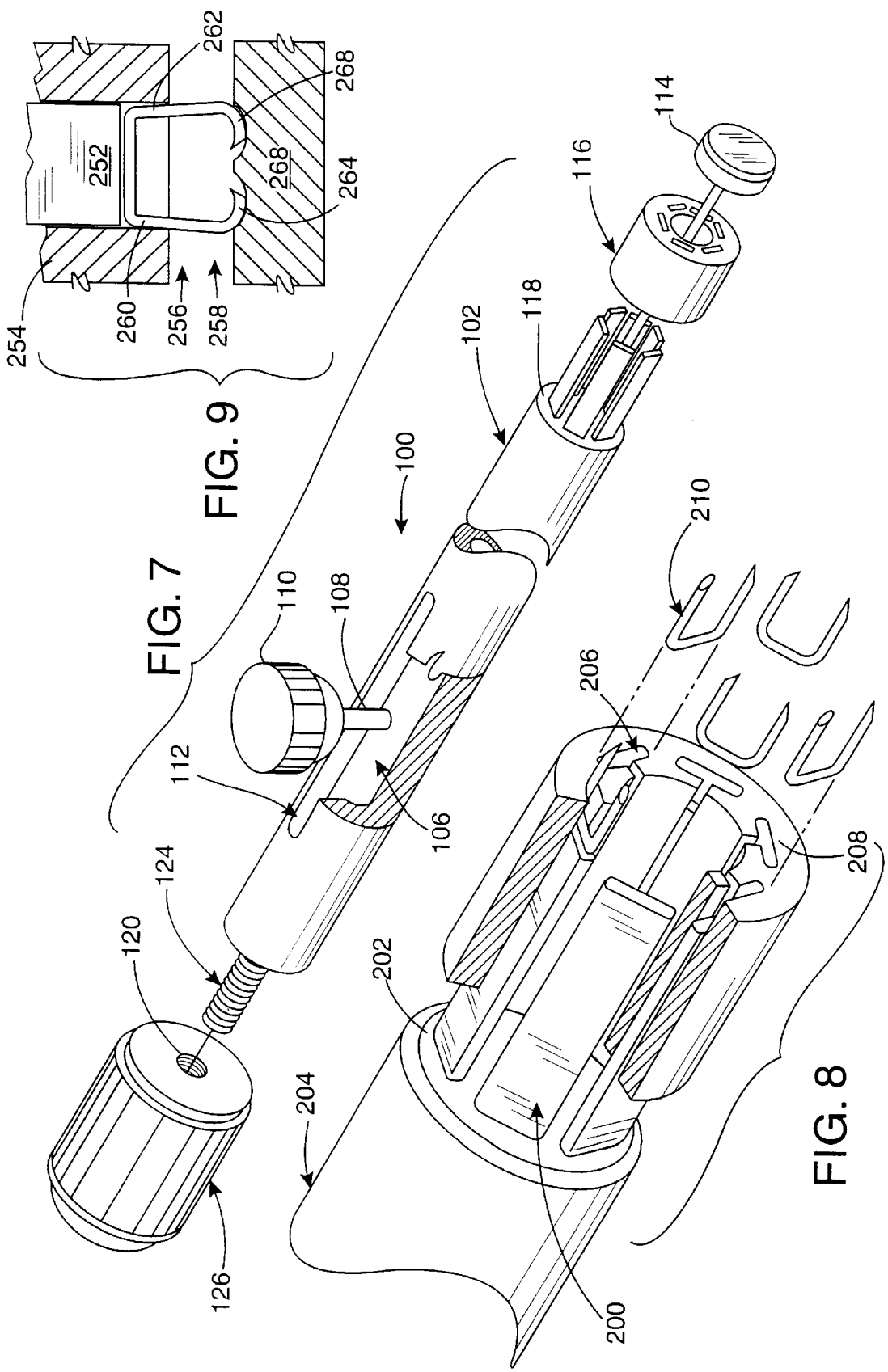

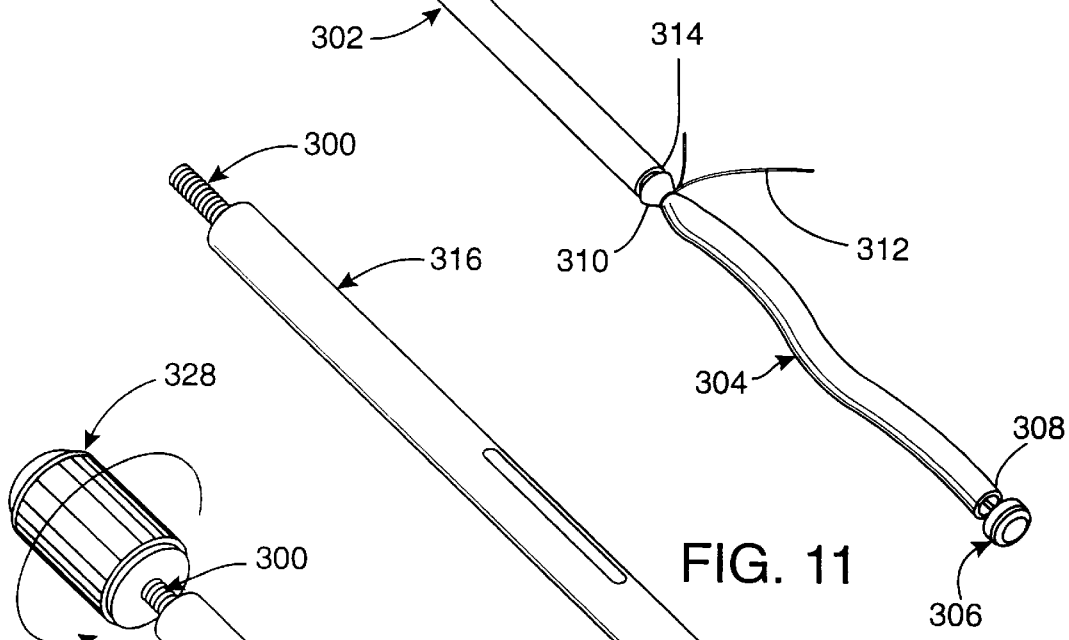
FIG. 10
FIG. 11
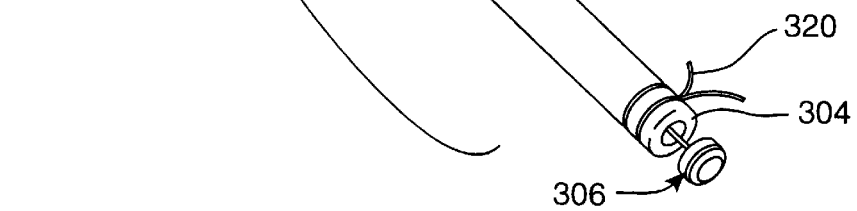
FIG. 12

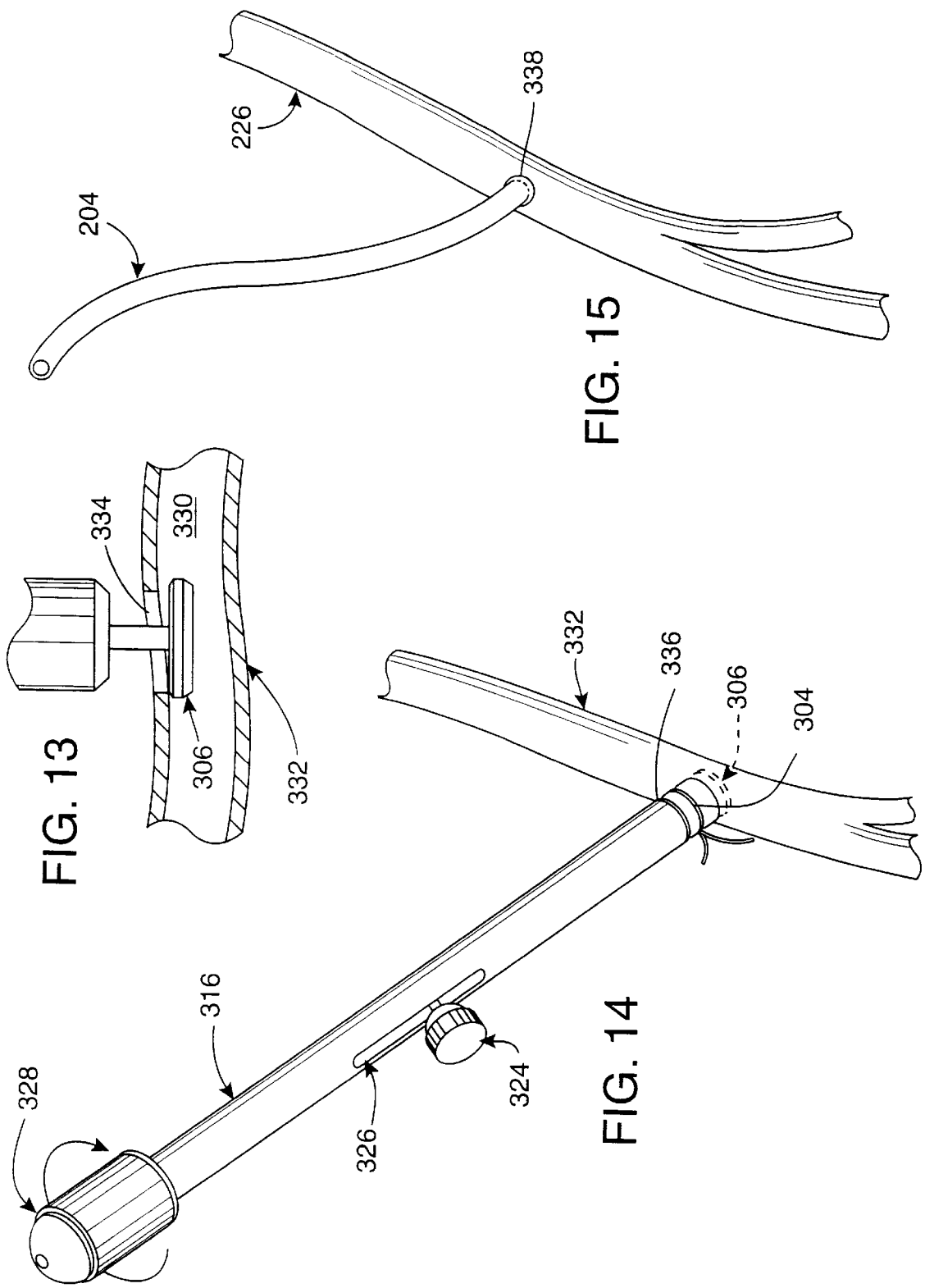

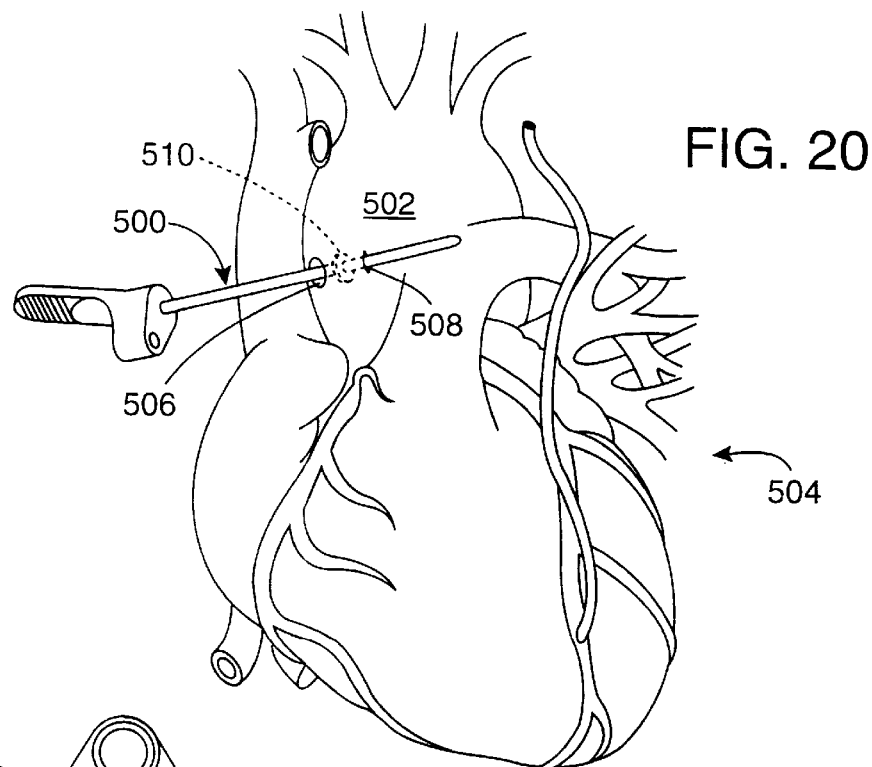
FIG. 20
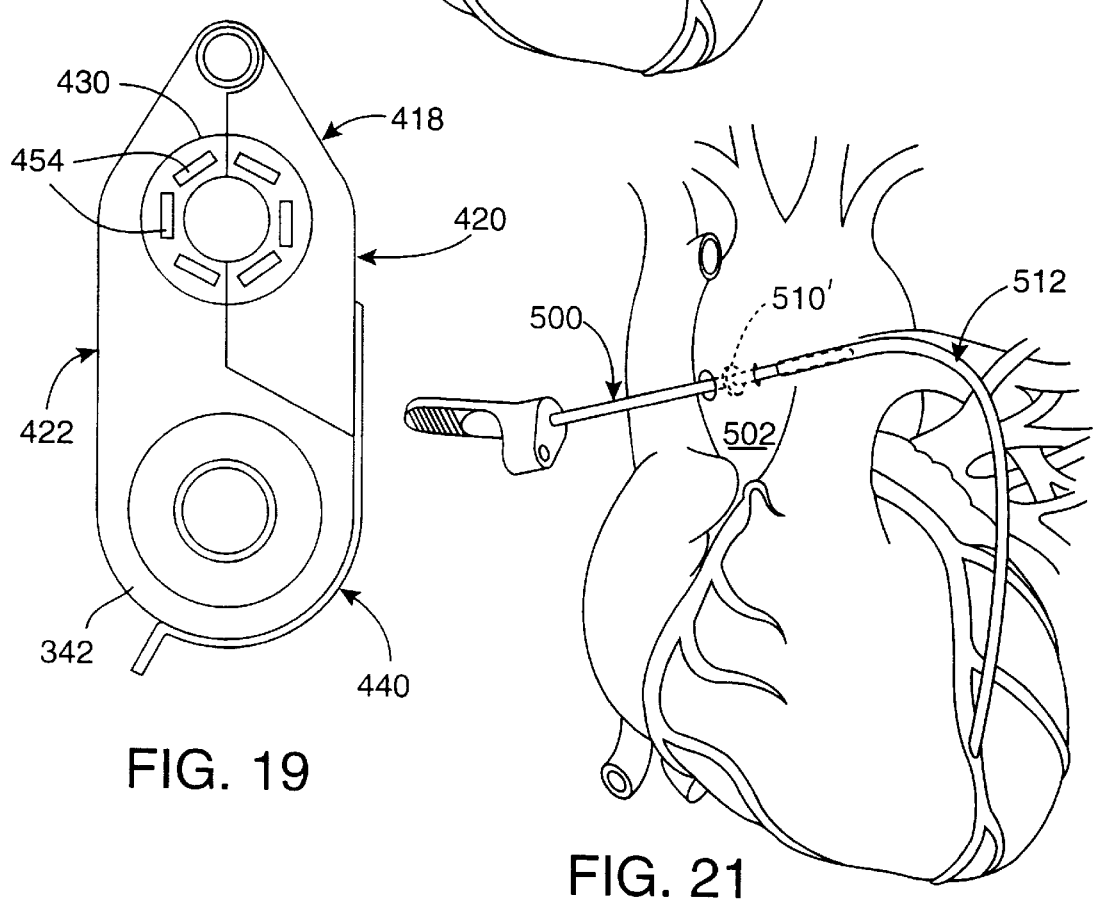
FIG. 19
FIG. 21

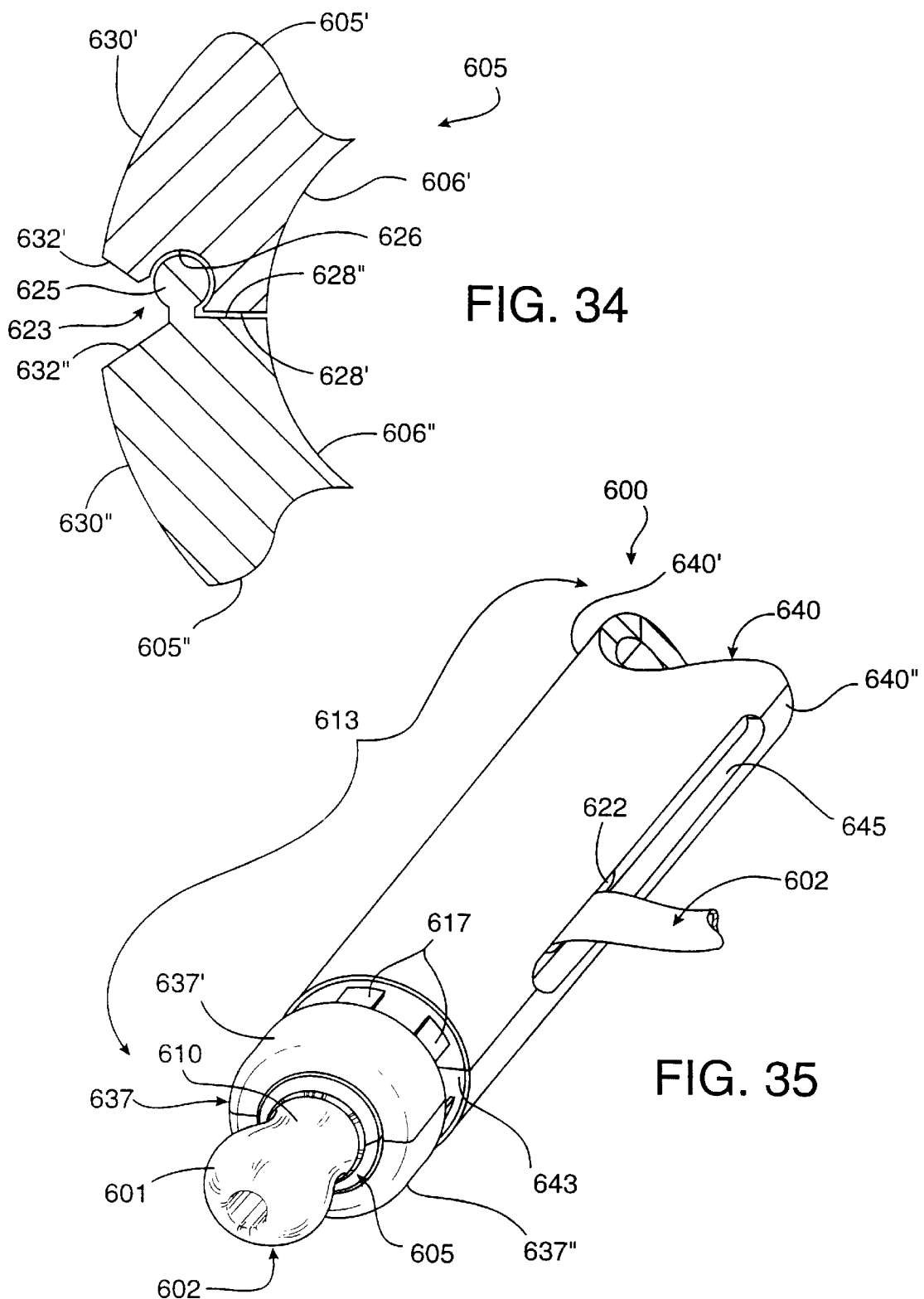

SURGICAL ANASTOMOSIS APPARATUS AND METHOD THEREOF

CROSS REFERENCE TO RELATED APPLICATIONS

This application is a continuation of U.S. patent application Ser. No. 09/488,140, filed Jan. 20, 2000, now U.S. Pat. No. 6,176,413, which is a divisional of U.S. patent application Ser. No. 09/267,247, filed Mar. 12, 1999, now U.S. Pat. No. 6,253,984, which is a division of U.S. patent application Ser. No. 08/979,831 filed Nov. 20, 1997, now issued as U.S. Pat. No. 5,881,943, which is a continuation of application Ser. No. 08/759,110 filed Dec. 2, 1996, now abandoned, which is a continuation-in-part of application Ser. No. 08/550,285, filed Oct. 31, 1995, now issued as U.S. Pat. No. 5,709,335, which is a continuation of application Ser. No. 08/261,167, filed Jun. 17, 1994, now abandoned. The complete disclosures of these applications are hereby incorporated herein by reference.

FIELD OF THE INVENTION

The invention relates generally to surgical stapling appliances and more particularly to an improved apparatus and method for the anastomotic surgical stapling of luminal organs, such as vascular lumens.

BACKGROUND OF THE INVENTION

Various instruments are known in the prior art for end-to-end and end-to-side anastomotic surgical stapling together of parts of the alimentary canal (i.e., esophagus, stomach, colon, etc.). These instruments employ staple cartridges, generally in the shape of a hollow cylinder, of different sizes to accommodate tubular organs of varying diameters. End-to-end and end-to-side anastomoses are achieved by means of at least one ring of surgical staples.

The traditional technique for surgical stapling anastomosis is to position the stapling cartridge within the tubular organ to be stapled. The cut end of the tubular organ is inverted (i.e., folded inwardly) over the annular end of the staple cartridge creating an inverting anastomosis upon stapling. An essential requirement of the inverting anastomotic technique is the incorporation of knives within the staple cartridge to trim excess tissue from the anastomotic connection.

The prior art anastomotic stapling instruments form generally circular anastomotic connections, and have been largely limited to alimentary organs. With respect to end-to-side vascular anastomosis, circular connections, rather than an elliptical connections, are sometimes disadvantageous as they are less phvsiologic or natural. This unnatural connection may create turbulence in the blood flow as it courses through the anastomosis, damaging the intima (i.e., inner wall) of the blood vessel and predisposing it to forming blood clots.

In the present state of the art, end-to-end and end-to-side anastomosis between blood vessels have typically been accomplished by hand-sewn suturing techniques. These techniques are time consuming, not as reliable as stapling, and subject to greater human error than stapling. Current stapling instruments used for alimentary canal are not suitable, however, for vascular anastomosis due to their large to sizes and inability to provide non-circular and low turbulence anastomoses. A typical prior art instrument has a circumference of approximately 8 cm (3 in), far too thick to accommodate coronary arteries and veins, which have circumferences ranging from 0.50 to 1.0 cm and from 1.5 to 2.5 cm, respectively.

An additional drawback of prior stapling instruments is the inability to provide an everted (i.e., folded outwardly) anastomosis. An inverted vascular anastomosis would expose the cut ends of the blood vessels to the vessel lumen and could lead to the formation of blood clots. For this reason, hand-sewn everted anastomoses for vascular connections are preferable, despite time and reliability drawbacks.

Accordingly, it is a general object of the present invention to provide an improved instrument and method for vascular anastomosis.

It is also an object of the present invention to provide a surgical anastomosis apparatus small enough to accommodate vascular lumens.

Another object of the present invention is to provide a surgical anastomosis apparatus for everted anastomosis.

Another object of the present invention is to provide a method for surgical stapling that does not require the removal of excess tissue from the anastomotical connection.

Still another object of the present invention is to provide an instrument and method for vascular anastomosis that is less time-consuming and more reliable than the prior art.

SUMMARY OF THE INVENTION

The present invention provides a novel instrument and method for vascular anastomoses which overcomes the drawbacks of prior art designs and achieves the aforesaid advantages.

Very generally, the surgical stapling instrument of the present invention is for stapling a tubular tissue structure having at least one distal end to a luminal structure, such as a vascular lumen or another tubular tissue structure. The instrument comprises a rod having a circumference sufficient to pass within the tubular tissue structure, an anvil mounted on the rod, and a generally tubular staple cartridge for containing a plurality of staples. The anvil has an array of staple deforming means thereon and is of a size sufficient to pass through a surgically formed opening in and to be accommodated within the luminal structure. The inner passage of the staple cartridge is sufficient to axially accommodate the tubular tissue structure between the rod and the inner surface of the staple cartridge, and sufficient to allow the staple cartridge to be moved axially along the rod. The staple delivery end of the staple cartridge is positioned toward the staple deforming means of the anvil and has an outer dimension small enough so that the tubular tissue structure can be everted thereover. A clamping mechanism secures the everted portion of the tubular tissue structure and the luminal structure adjacent to the surgically formed opening between the staple cartridge and the anvil. A plurality of staples may then be ejected to pass through the everted portion of the tubular tissue structure and the luminal structure to engage the staple deforming means to deform the staples and create a bond between the tubular tissue structure and the luminal structure.

In another aspect of the present invention, an end-to-side surgical anastomosis apparatus is provided for stapling an end of a tubular tissue structure to a side of a luminal structure. The anastomosis apparatus includes an elongated housing defining a central bore extending longitudinally therethrough and terminating at a bore opening at a distal end of the housing. The central bore includes a transverse cross-sectional dimension sufficiently sized and configured for receipt of the tissue structure therein in a manner positioning the end of the tissue structure through the bore opening. The elongated housing further includes an eversion support surface extending circumferentially about the bore opening adjacent the distal end. This surface is configured to retain and support an everted end of the received tissue structure which extends through the bore opening to face an intimal surface of the tissue structure in an outward direction. The anastomosis apparatus further includes an anvil having a fastener engaging surface, and a compression device having a shoulder portion formed for selectively compressing the everted end of the tissue structure and a surface of the luminal structure together against the fastener engaging surface. The compression device is further formed to deform the fasteners into contact with the everted end of the tubular tissue structure and the luminal structure to create an anastomotic bond between the tubular tissue structure and the luminal structure.

At least one driver pin is preferably provided moveable relative to the compression device for ejecting the plurality of fasteners through the everted end of the tubular tissue structure and the luminal structure to engage the fastener engaging surface. This engagement deforms the fastener and creates a bond between the tubular tissue structure and the luminal structure.

In still another aspect of the present invention, a method of end-to-side surgical anastomosis is provided between a tubular tissue structure, having at least one end, and a luminal structure, such as a vascular lumen or another tubular tissue structure. The method includes the steps of A) inserting the tubular tissue structure in to a central bore of an anastomosis apparatus, and B) everting an end of the tubular tissue structure over and against an eversion support surface of the anastomosis device and at a distal end of the central bore to an everted condition positioning an intimal surface of the everted end in a direction facing outwardly. The next steps of the present invention include C) positioning the everted end of the tubular tissue structure and a surface of the luminal structure between an anvil and an opposed shoulder of a compression device of the anastomosis apparatus, and D) contacting the intimal surface of the everted end with a surface of the luminal structure adjacent a surgically formed opening therein. Finally, the last step of the method of end-to-side surgical anastomosis of the present invention includes E) applying a plurality of fasteners to the everted end of the tubular tissue structure and the surface of the luminal structure to contact the anvil and deform the fasteners to form an anastomotic bond therebetween.

DETAILED DESCRIPTION OF THE DRAWINGS

The procedure and system of the present invention have other objects and features of advantage which will be readily apparent form the following description of the Best Mode of Carrying Out the Invention and the appended claims. when taken in conjunction with the accompanying drawings, in which:

FIG. 1 is a fragmentary side elevation view, in cross section, of one embodiment of the anastomosis device constructed in accordance with the present invention and illustrating an end of the tubular tissue structure everted over the device end.

FIG. 2 is a front elevation view, in cross-section, of the anastomosis device taken substantially along the plane of the line 3—3 in FIG. 1

FIG. 3 is a rear elevation view, in cross-section, of the anastomosis device taken substantially along the plane of the line 2—2 in FIG. 1

FIG. 4 is a side elevation view, in cross-section, of the anvil of the anastomosis device taken substantially along the plane of the line 4—4 in FIG. 3

FIG. 7 is an exploded top perspective view, partially cut-away, of the anastomosis device of FIG. 1.

FIG. 8 is an enlarged, exploded, top perspective view, partially cut-away, of a staple cartridge assembly of the anastomosis device of FIG. 1.

FIG. 9 is an enlarged, side elevation view, in cross-section, of the anvil and staple cartridge assembly of the anastomosis device of FIG. 1 illustrating the deformation of a staple.

FIGS. 10–12 is a sequence of top perspective views illustrating the loading of a tubular tissue structure in the anastomosis device of FIG. 1

FIG. 13 is an enlarged, side elevation view, in partial cross-section, showing the positioning of the anvil of the anastomosis device through a luminal structure.

FIG. 14 is a reduced top perspective view of the anastomosis device of FIG. 1 mounted to the luminal structure.

FIG. 15 is a reduced top perspective view of the tubular tissue structure anastomotized to the luminal structure using the anastomosis device of FIG. 1.

FIG. 19 is an end view of the staple cartridge assembly of FIG. 18.

FIGS. 20–22, 24, 25, 27 and 28 is sequence of top perspective views illustrating the application of the alternative embodiment anastomosis device of FIG. 17 for proximal anastomosis of the crafted tubular tissue structure to the ascending aorta.

FIG. 34 is a fragmentary, enlarged top plan view of a hinge assembly of the anastomosis device of FIG. 29.

FIG. 35 is a fragmentary, top perspective view of the anastomosis device of FIG. 29 and illustrating the tubular tissue structure everted over the distal end of the eversion mandrel.

DETAILED DESCRIPTION OF THE INVENTION

Figure 5:
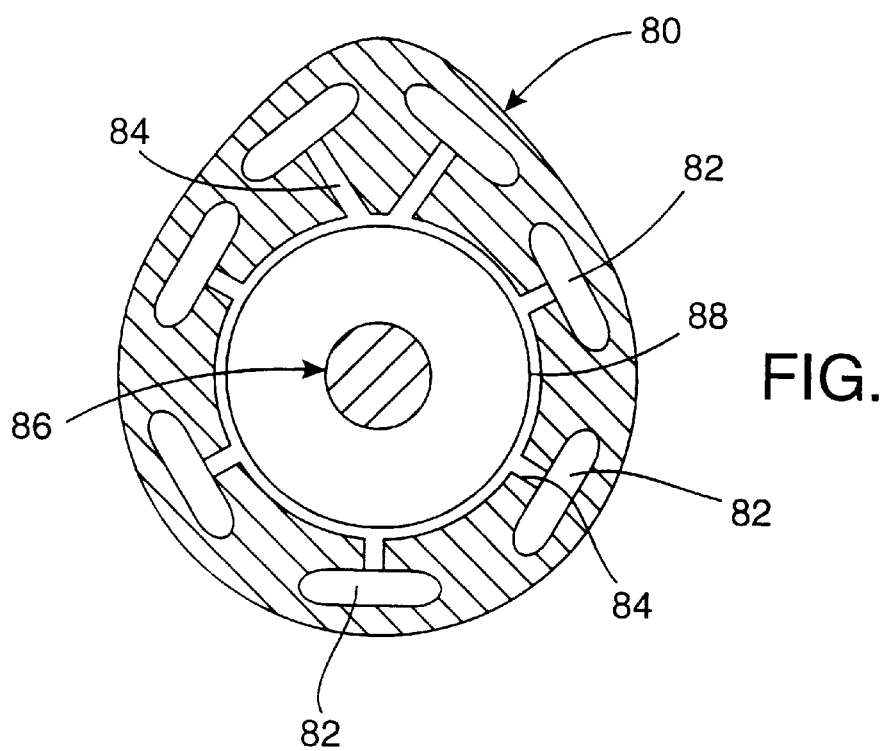
FIG. 5 is a front elevation view, in cross-section, of an alternative embodiment of FIG. 3 illustrating a tear drop-shaped configuration.

Reference will now be made in detail to the preferred embodiments of the invention. The present invention provides methods and devices for performing surgical interventions within the heart or a great vessel such as the aorta, superior vena cava, inferior vena cava, pulmonary artery, pulmonary vein, coronary arteries, and coronary veins, among other vessels. While the specific embodiments of the invention described herein will refer to a closed-chest surgical procedure and system for the treatment of medically refractory atrial fibrillation, it should be understood that the invention will be useful in performing a great variety of surgical procedures requiring the ablation of tissue structure, including surgical treatment of Wolfe-Parkinson-White (WPW) Syndrome, ventricular fibrillation, congestive heart failure and other procedures in which interventional devices are introduced into the interior of the heart, coronary arteries, or great vessels. Advantageously, the present invention facilitates the performance of such procedures through percutaneous penetrations within intercostal spaces of the rib cage, eliminating the need for a median sternotomy or other form of gross thoracotomy. However, as will be apparent although not preferred, the system and procedure of the present invention could be performed in an open-chest surgical procedure as well.

Referring to FIGS. 1–7, there is shown a structural embodiment of the present invention which is best suited for anastomotic stapling of a tubular vessel having two distal or untethered ends. As will be evidenced by the detailed description below, this embodiment, i.e., distal stapler, is ideal for use during cardiopulmonary bypass surgery for making the primary anastomotic connection of a bypass vein to a coronary artery or to the aorta.

Referring now to FIG. 1, a portion 10 of the wholly configured distal stapler of the present invention, as shown in FIG. 7, comprises an elongated central rod 12 with anvil 14 mounted at its distal end 16. Anvil 14 is in the form of a circular, elliptical or tear drop-shaped disk and is mounted, by suitable means such as welding, to the end of central rod 12 transversely thereof and at the center of the anvil. The edges of anvil 14 are beveled or otherwise generally rounded to enable anvil 14 to slip easily through incisions in vascular walls—much like a button through a button hole.

The central rod 12 has a circumference sufficient to permit the rod to axially extend through a tubular vessel, indicated in phantom at 20, to be stapled. Central rod 12 also axially extends within tubular housing 22, driver pins 24 and staple cartridge 26, together forming a contiguous shaft 28 having an inner circumference sufficient to accommodate tubular vessel 20 sandwiched between them and central rod 12. Staple cartridge 26 has an outer circumference sufficient to accommodate everted end 34 of tubular vessel 20. Lip 36 of cartridge 26 is tapered to facilitate eversion of tubular vessel 20. Anvil 14 has circumference of a size equivalent to the outer circumference of staple cartridge 16.

Circumferences of vascular vessels range from 0.50 to 1.0 cm for coronary arteries and from 1.5 to 2.5 cm for veins. Accordingly, all circumferences, discussed above of stapler 10 are of a size to optimally coaxially accommodate the vein to be stapled.

The end of central rod 12 opposite anvil 14 is centrally mounted. preferably welded, on a cylindrical base 40 which extends coaxially within tubular housing 22 (as shown in FIG. 7 by reference number 106) and has a circumference sufficient to be slidable within tubular housing 22. The accommodated tubular vessel 20 extends along central rod 12 to cylindrical base 40. Provided on the surface of central rod 12 proximal to base 40 is circumferential groove 44 for facilitating the securing of tubular vessel 20 to rod 12 by means of string 46. Similarly, circumferential groove 48 and string 50 are provided to secure everted end 34 of vessel 20 to staple cartridge 26. An alternative embodiment of staple cartridge 26 for securing an everted vein comprises tiny hooks around the circumference at end 36 of the cartridge. Other suitable means for accomplishing the securing function may be used as well.

Referring now to FIG. 2, there is shown a cross-sectional view of stapler 10 of the present invention in the direction of arrows 2—2 of FIG. 1. Here. the staple delivery end 60 of a circular staple cartridge is illustrated encasing a circular array of staple delivery means or staple shafts 62. The present invention is not limited to a single staple shaft array, however. It is commonly known in the art to employ a plurality of concentric arrays or rows of staple shafts for anastomotic procedures. Extending from staple shaft array 62, is an array of narrow channels 68, each narrow channel corresponding to each staple shaft. Channel array 68 is used solely for manufacturing purposes and is not a necessary element of the invention. Central rod 64 and its base 66 are axially and centrally located within the cylindrical staple cartridge 60.

FIG. 3 shows the underside view of anvil 70 in the direction of arrows 3—3 of FIG. 1. The anvil 70 has an array 74 of means for deforming staples. Central rod attachment 72 is centrally located on anvil 70 which provides an array of staple deforming means 74, comprised here of an array of recess pairs, for bending staples projected from corresponding array of staple shafts 62 of the staple cartridge of FIG. 2.

Depicted in FIG. 4 is a cross-sectional view of anvil 70 in the direction of arrows 4—4 of FIG. 3. Each recess pair 76 is curved to bend staple legs radially inward. The projected staples can be made to bend radially inward or radially outward depending on the spacing 78 between the recess of each paired recess 76. Alternatively, each recess can be positioned orthogonal to its present position to bend the staple legs at right angles to their axis of projection.

Figure 6:
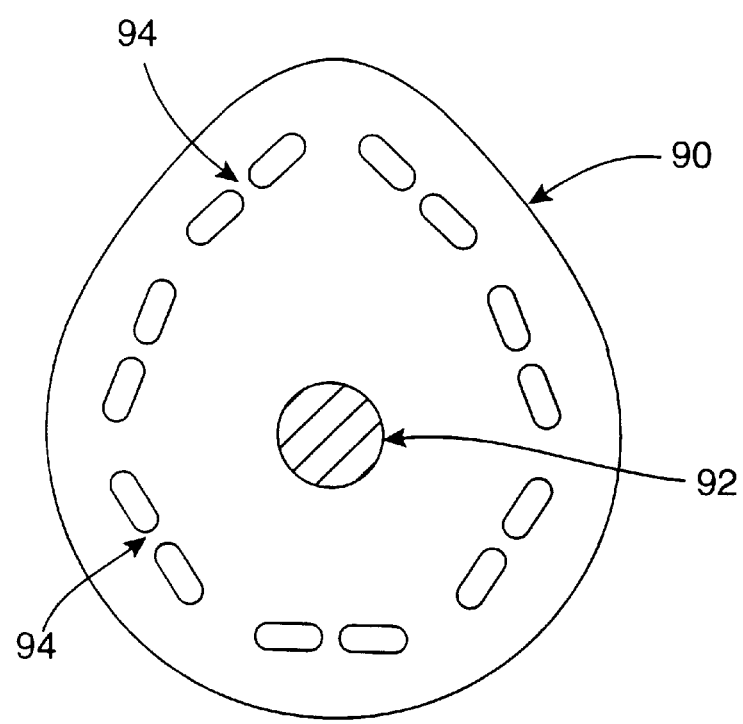
FIG. 6 is a rear elevation view, in cross-section, of the anvil of the alternative embodiment of FIG. 5 taken substantially along the plane of the line 2—2 in FIG. 1

Although the present invention is primarily described and depicted as forming staple bonds that are circular and as having component circumferences that are circular, other embodiments are realized for forming staple bonds having elliptical, tear drop or other generally oval circumferences. Accordingly, the anvil and associated staple recess array, and the cartridge housing and associated staple shaft array of these alternative stapler embodiments have circumferences in the shape of the desired staple bond. For example. FIGS. 5 and 6 illustrate an anvil and staple cartridge, respectively, having tear-drop shaped circumferences.

FIG. 5 shows a cross-sectional view of a tear-drop shaped staple cartridge. The staple delivery end 80 of the staple cartridge is illustrated encasing a tear drop array of staple delivery means or staple shafts 82. Extending from staple shaft array 82, is an array of narrow channels 84, each narrow channel corresponding to each staple shaft. Channel array 84 is used solely for manufacturing purposes and is not a necessary element of the invention. Central rod 86 and its base 88 are coaxially and centrally located within the cylindrical portion of dear drop staple cartridge 80.

FIG. 6 shows the underside view of a tear drop shaped anvil 90. Central rod attachment 92 is centrally located on the circular portion of anvil 90 which provides an array of staple deforming means comprised of recess pairs 94 for bending staples projected from corresponding array of staple shafts 82 of the staple cartridge of FIG. 5.

Referring now to FIG. 7, there is shown stapler 100 of the same embodiment depicted in FIGS. 1–4. A tubular housing 102 coaxially contains central rod 104 and rod base 106, the end of central rod 104 opposite that of anvil 114 being suitably mounted, such as by welding, to rod base 106 (connection not shown). Threadedly mounted to and extending perpendicular from rod base 106 is a short stem 108, positioned at approximately half the length of base 106. The top of stem 108 has cylindrical knob 10 transversely mounted. Stem 108 is moveable within narrow channel 112, cut within housing 102 and running parallel to the axis traveled by central rod 104 and rod base 106. Channel 112 limits the rotational movement of stem 108 and thereby maintains a proper radial orientation between anvil 114 and staple cartridge 116 during reciprocation.

Weldedly mounted to and protruding perpendicularly from cylindrical face 118 of housing 102 and paralleling rod 104 is cylindrical array of staple driver pins 120, all drivers pins being identical and each having the form of a solid parallelogram. Staple cartridge 116 encases, from end to end, cylindrical array of hollow staple shafts 122 which holds a plurality of preloaded staples (not pictured). All shafts 122 are identical and each has height and width dimensions such that a corresponding staple driver pin 120 is slidable therein.

In order to have an optimally functioning stapler, it is necessary to maintain a clean and clear passageway for central rod 104, base 106 and staple shafts 122. Accordingly, one embodiment of the present invention comprises a disposable cartridge which is disposed of and replaced after one anastomotic stapling. Another embodiment provides a slidable sleeve around the driver pin array to prevent blood and tissue from getting caught therein.

For anastomosis to be successful, it is imperative not to injure the living tissue being stapled by overcompressing it between anvil 114 and staple cartridge 116 or by a staple bond that is exceedingly tight. Accordingly, overcompression of the tissue is prevented in the present invention by limiting the length of driver pins 120. Other embodiments are known in the prior art for accomplishing this objective. For example. U.S. Pat. No. 4,573,468 employs mutually coacting stops located on the inner surface of a tubular housing and on the surface of a coaxial rod to provide variable degrees of engagement between tissues to be stapled so as to ensure against overcompression of the tissue. A spring-loaded engagement between the rod and tubular housing is also applicable for the present invention. Other means suitable for this purpose will be apparent to those having ordinary skill in the art.

Finally, FIG. 7 illustrates threaded end 124 of rod base 106 which extends beyond the length of housing 102 to threadedly engage with cylindrical nut 126 which has internally threaded throughbore 128 extending the full length of cylindrical nut 126 to allow end 124 to exit therethrough.

FIGS. 8 and 9 illustrate the mechanical interaction between the staple driver, staple cartridge and anvil upon engagement. FIG. 8 illustrates staple driver array 200 mounted on face 202 of tubular housing 204 sildably engaged within staple shaft array 206 of staple cartridge 208. Staple array 210 is projected from staple cartridge 208 and through the tissues to be stapled (not shown). FIG. 9 shows a close-up of a staple being driven by driver pin 252 and projecting through cartridge 254 through tissues 256 and 258. The legs 260 and 262 of staple 250 then engage with and bend along the curved recesses 264 and 266, respectively, of anvil 268 to form a bond between tissues 256 and 258.

Referring now to FIGS. 10–16, with like numbers referring to like elements, there is illustrated the steps of the anastomotic procedure using the to structural embodiment described above. Now referring to FIG. 10 specifically, the anvil-headed end of rod base 302 is inserted into transected vein 304 having a length in the range of 10–18 cm (4–7 inches). End 308 (the end to be stapled) of vein 304 is positioned proximate to anvil 306. Opposing end 310 of vein 304 is tied with string 312 to central rod 314 at a circumferential depression (not shown) proximate to base 302.

FIG. 11 shows the step of inserting central rod 314 with attached vein 304 into staple cartridge 318 and tubular housing 316 such that staple cartridge 318 is proximate to anvil 306. FIG. 12 illustrates the next several steps of the method of the present invention which can be performed in any order. The end of vein 304 is everted over staple cartridge 318 and tied with string 320 securing it to staple cartridge 318 (covered by vein 304). Threaded stem 322 of cylindrical knob 324 is threadedly engaged with a threaded bore (not shown) base 302, the bore being aligned with narrow channel 326. Cylindrical nut 328 is threadedly engaged with the threaded end 300. As indicated in FIG. 13, anvil 306 is positioned within lumen 330 of vascular artery 332 via incision 334. A cross-section of a portion of vein 304 is shown everted over the staple delivery end of staple cartridge 318.

In FIG. 14, central rod 314 (not visible) and rod base 302 (not visible) are optimally coaxially positioned within tubular housing 316 by means of sliding knob 324 along channel 326 toward vascular artery 332. Nut 328 is rotated in a clockwise direction to engage it with tubular housing 316 causing rod base 302 to become rigidly interconnected with nut 328. As the clockwise turning continues, rod base 302 is drawn through the bore in nut 328, bringing the staple cartridge 336 and anvil 306 within artery 332 together. An embodiment employing mutually coacting stops (not shown) would, at this point, be at the first coacting position or the "loaded" position. The clockwise motion is continued so that everted vein 304 engages with the wall of artery 332 and until the staple drivers (not visible) are actuated, driving the staples (not visible through the tissues to create a bond 338 (FIG. 15). If mutually coacting stops are employed, the configuration would be in the "firing" position.

Figure 16:
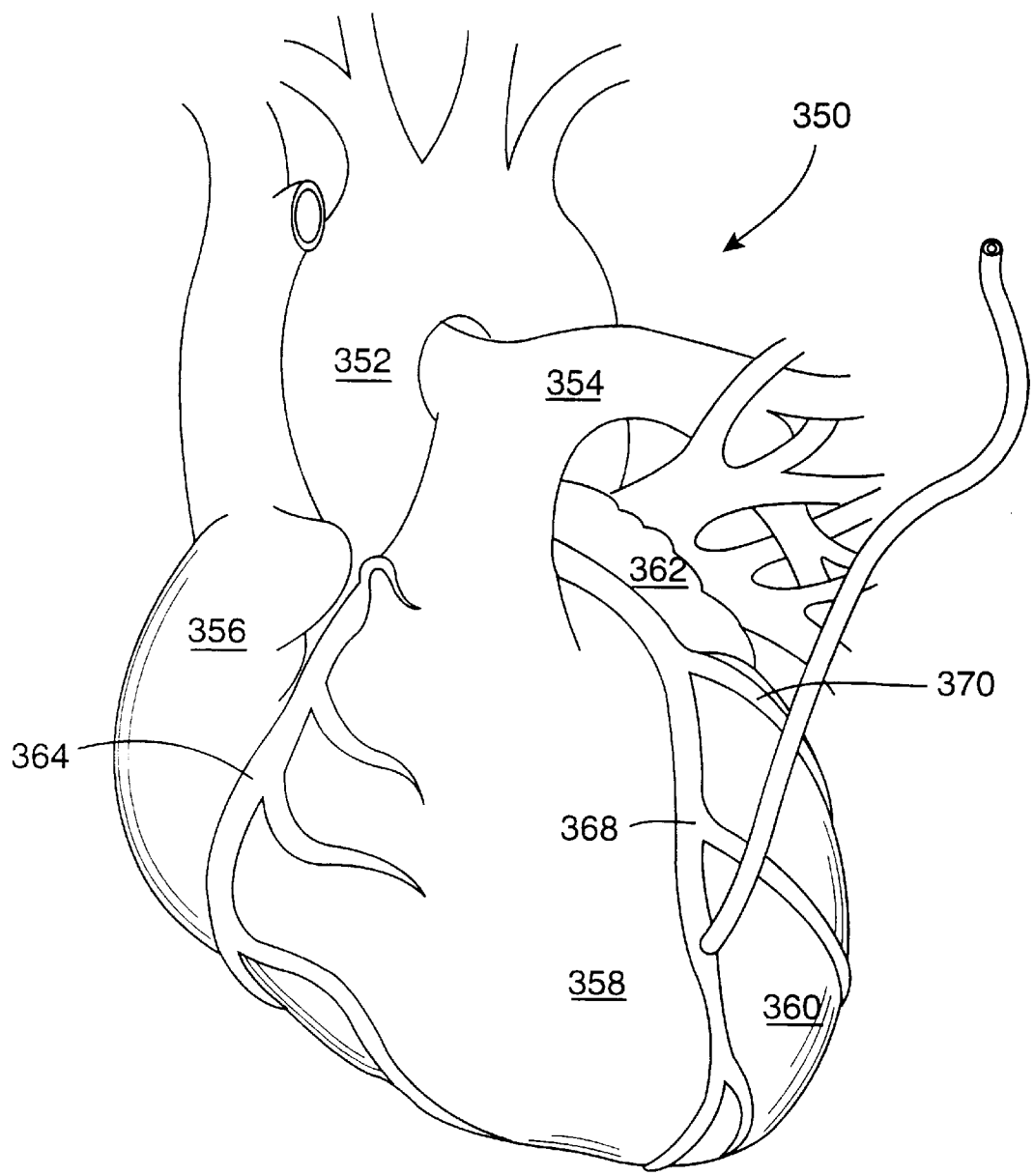
FIG. 16 is a front elevation view of a grafted tubular tissue structure anastomotized to a coronary artery of the heart through the anastomosis device of FIG. 1.

Finally, FIG. 16 illustrates heart 350 having, aorta 352, pulmonary artery 354, right atrium 356, right ventricle 358, left ventricle 360, left atrial appendage 362, right coronary artery 364, left anterior descending artery 368, and diagonal artery 370. Here, vein 304 has been anastomotically stapled to left anterior descending artery 368.

To complete the anastomotic procedure of the bypass vein 304, the unstapled end of the anastomotized vein 304 must now be connected to aorta 352. However, another structural embodiment of the present invention, referred to as the "proximal" stapler, is needed since the embodiment described above, i.e., the "distal" stapler, requires the vein to have two distal or untethered ends. Accordingly, FIGS. 17–28 describe a structure and method thereof for a second embodiment of the present invention which is suited for the anastomotic stapling of a tubular vessel having, only one distal end, the other end having already been anastomotically stapled.

Figure 17:
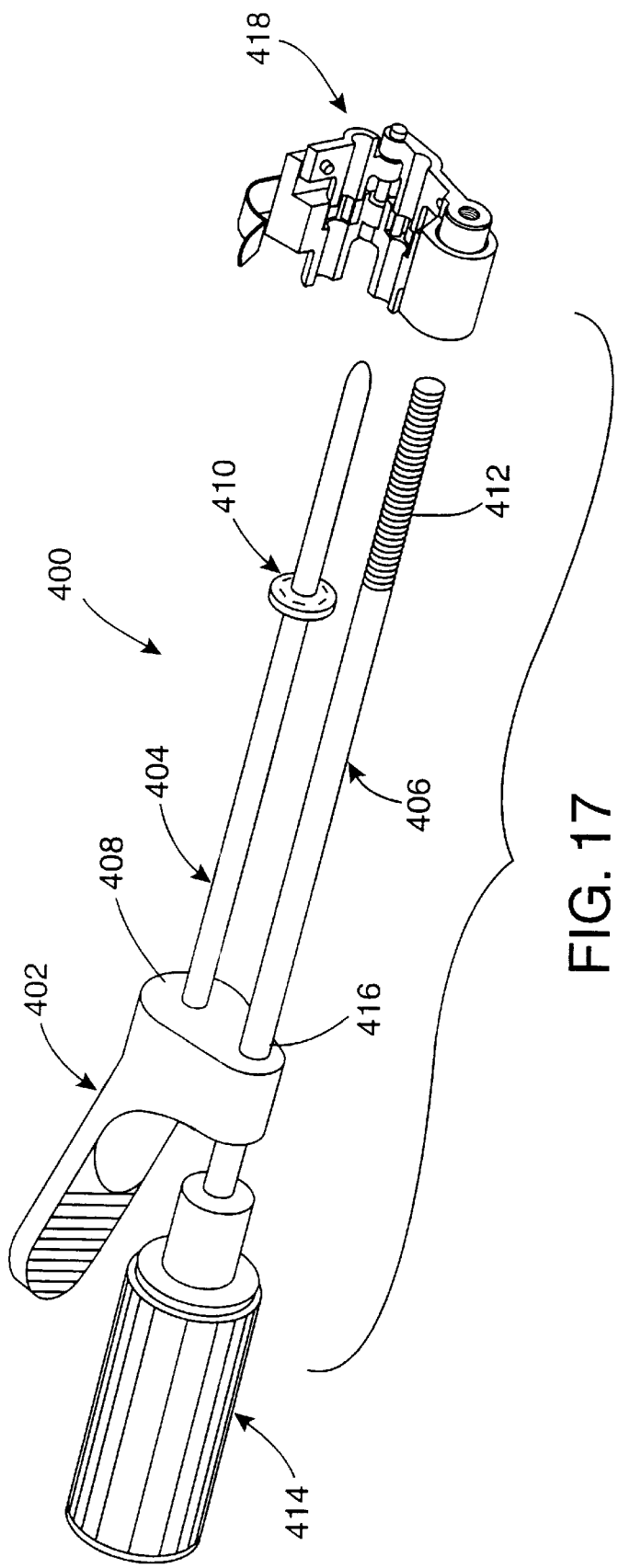
FIG. 17 is an exploded top perspective view of an alternative embodiment of the anastomosis device of the present invention.
Figure 18:
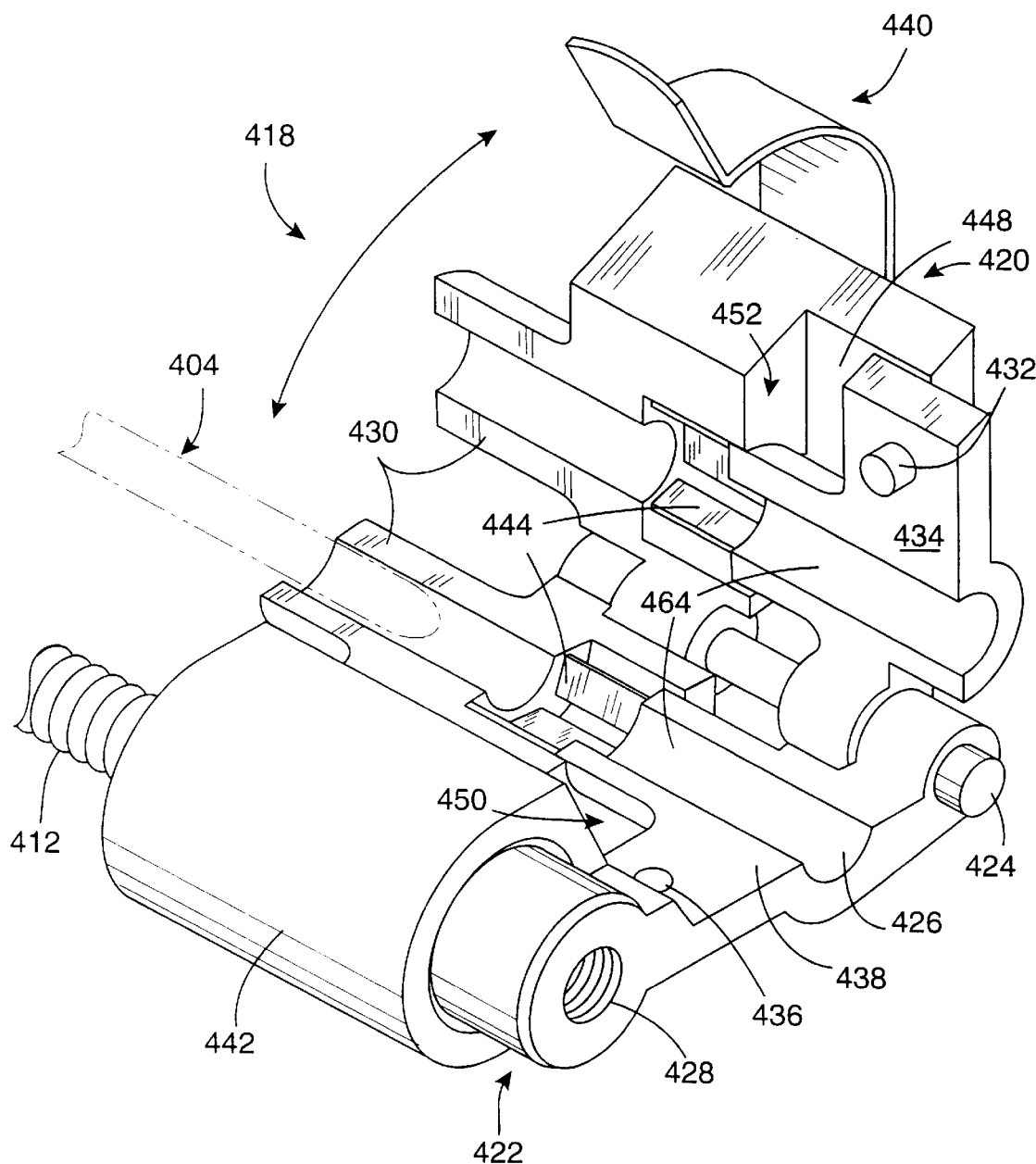
FIG. 18 is a fragmentary, enlarged top perspective view of a staple cartridge assembly of the alternative embodiment anastomosis device of FIG. 17.

Referring now to FIGS. 17–19, with like numbers referencing like elements, there is shown anastomotic stapler 400 having handle 402 with elongated vessel rod 404 and elongated driver rod 406 mounted perpendicularly to handle face 408 and parallel to each other, both being of approximately the same length. Vessel rod 404 has a centrally mounted generally circular anvil 410. Vessel rod 404 has a circumference sufficient to coaxially accommodate a tubular vessel (not shown) to be stapled to the aorta. Driver rod 406, having threaded end 412 and handle 414, extends through bore 416 of handle 402.

Stapler 400 also comprises staple cartridge 418, enlarged in FIG. 18 for purposes of describing its detail. Referring then to FIG. 18, there is shown the staple cartridge of FIG. 17 in its open position having top and bottom units 420 and 422, respectively. Units 420 and 422 are engaged at one side by hinge 424 which allows cartridge 418 to be opened and closed. Staple cartridge 4 18 has two parallel bores 426 and 428 with inner circumferences sufficient to coaxially accommodate vessel rod 404 with a coaxially accommodated vein (not shown) and driver rod 406, respectively. Staple delivery end 430 extends from staple cartridge 418 along, the axis of bore 426 to accommodate the everted end of a vein to be stapled. Bore 428 is internally threaded to be threadedly engagable with driver rod end 412.

For a proper fit between units 420 and 422, a detent-recess pair is provided having, detent 432 extending from inner surface 434 of top unit 420 which mates with recess 436 within inner surface 438 of bottom unit 4222. To secure closing. a curved clip 440 is provided to fit around cylindrical casino 442 of bore 428.

When in a closed position, staple cartridge 418 has cylindrical staple delivery means or staple shaft array (not shown) encased in staple delivery end 430 which mates with cylindrical driver pin array 444 mounted on driver 446. Both the hollow shafts and the solid driver pins have height and width measurements that allow them to be slidably engagable with each other. Driver 446 is slidable alone surface 448 of top unit 420 and surface 450 of bottom unit 422 to the point of engagement with shoulder 452 of top unit 420 upon which driver pin array 444 becomes engaged within the staple shaft array, projecting preloaded staples from the end of staple delivery end 430. Shoulder 452 limits the engagement of driver pin array 444 so that the tissue being stapled is not overcompressed. Modifications of the this embodiment can employ mutually coacting stops or spring-loaded type configurations between the driver and staple cartridge to prevent against overcompression of the tissue.

FIG. 19 shows a front view of staple cartridge 418 in its closed position with top unit 420 engaged with bottom unit 422. Clip 440 securely fits around cylindrical casing 442. Staple deforming end or staple shaft array 454 is shown on the face of staple delivery end 430.

FIGS. 20–28, with like numbers referencing like elements, depict the various steps of the anastomotic procedure using the structural embodiment in FIGS. 17–19 described above. Referring now to FIG. 20, vessel rod 500 is inserted through aorta 502 of heart 504 via incisions 506 and 508 on opposing walls of aorta 502 such that anvil 510 is centrally positioned within aorta 502.

Figure 22:
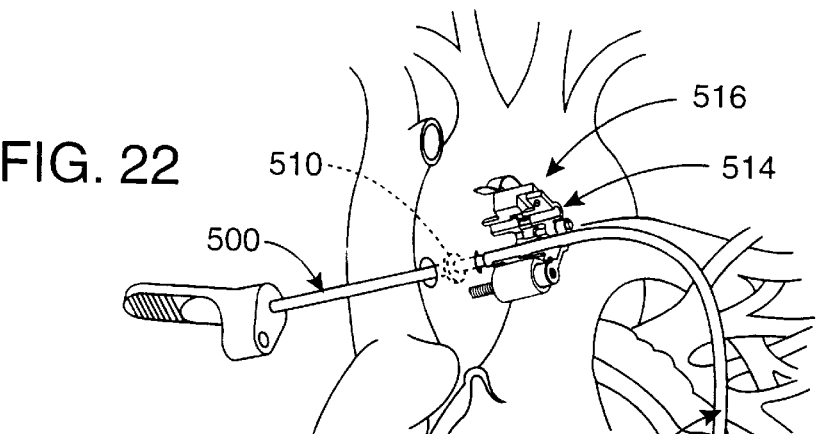
Figure 23:
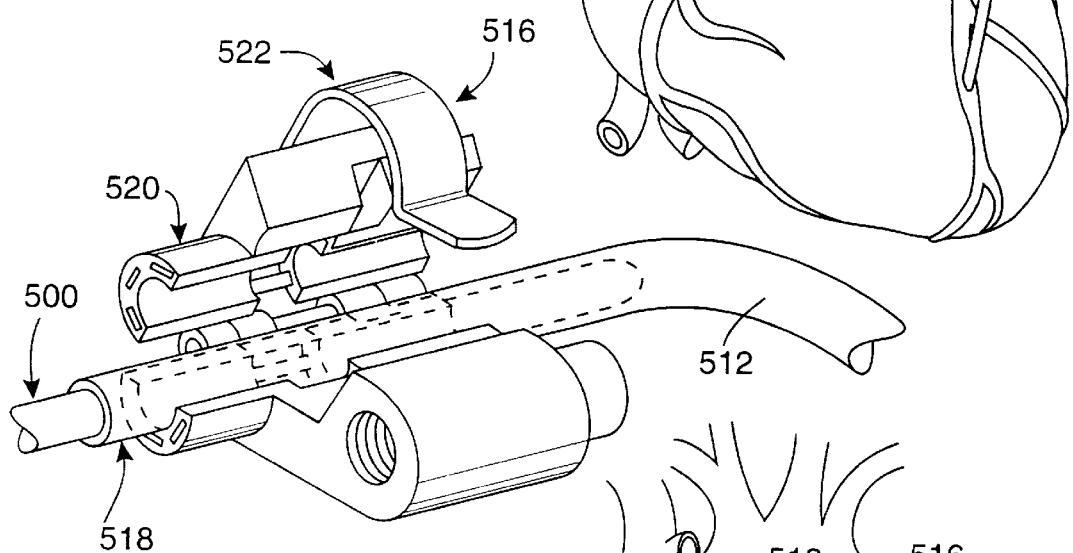
FIGS. 23 and 26 is a sequence of fragmentary, top perspective views illustrating the loading of a tubular tissue structure in the alternative embodiment anastomosis device of FIG. 17.
Figure 24:
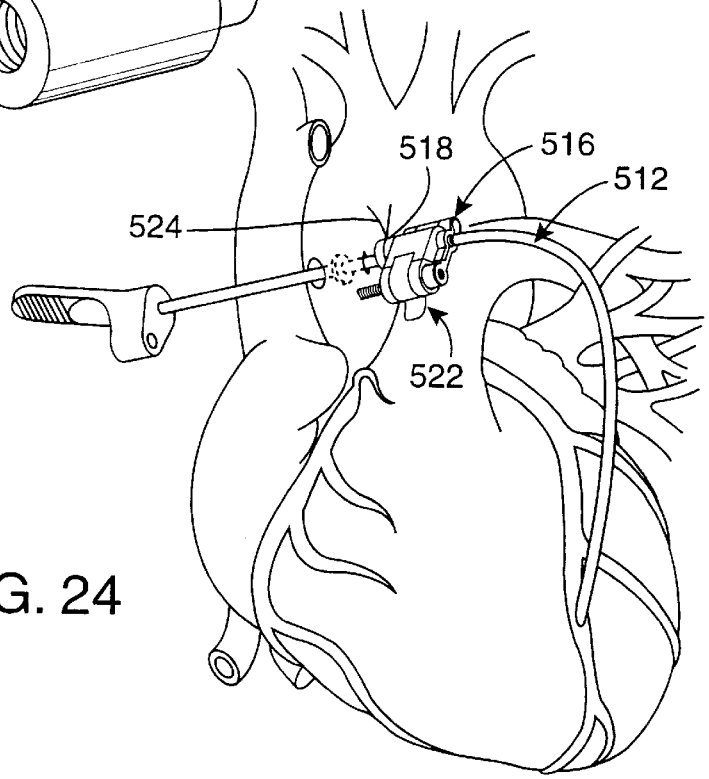

In FIG. 21, the end of vessel rod 500 is then inserted into the distal end of vein 512 with anvil 510 still centrally positioned within aorta 502. Next, as shown in FIG. 22, vessel rod 500 with accommodated vein 512 is positioned within the corresponding bore 514 in open staple cartridge 516. Rod 500 and vein 512 should be positioned such that a sufficient length of distal end 518 of vein 512 extends beyond the end of cartridge 516 such that distal end 518 can be everted over cylindrical sleeve 520 of cartridge 516 (See FIG. 23). Once vein 512 has been optimally positioned, staple cartridge 516 is clamped around it and secured with clip 522, illustrated in FIG. 24. Now, distal end 518 of vein 512 is everted over sleeve 520 and is securely tied with string 524.

Figure 25:
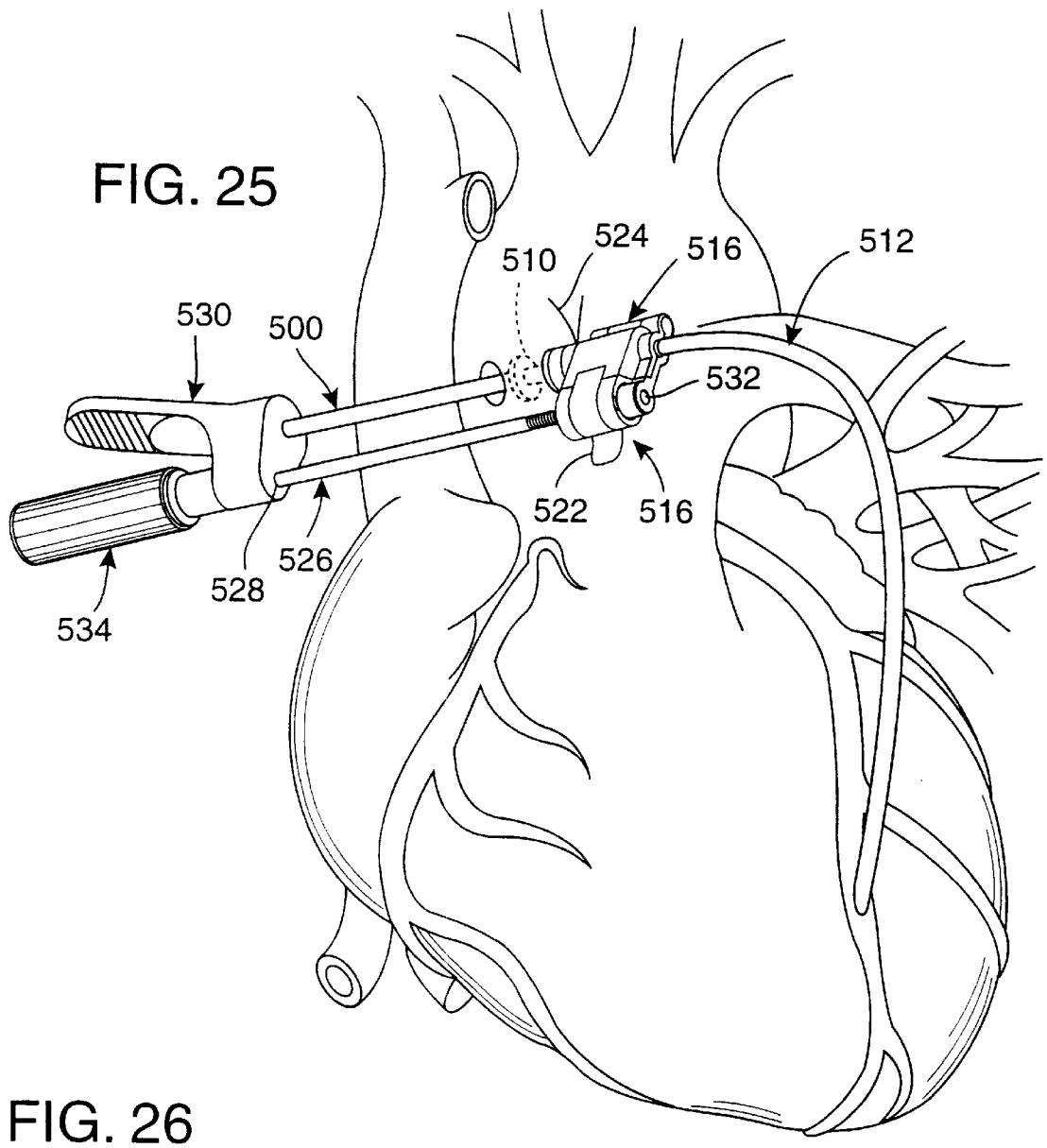
Figure 26:
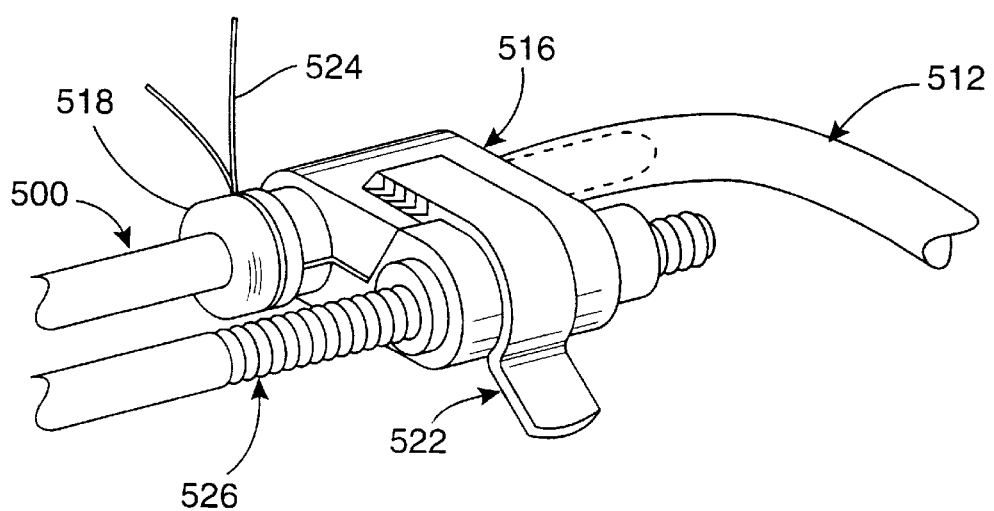

Referring now to FIG. 25, driver rod 526 is slid into bore 528 of handle 530 and then threadedly engaged with bore 532 of staple cartridge 516. FIG. 26 shows a close-up of staple cartridge 516 as it appears in its closed position.

Figure 27:
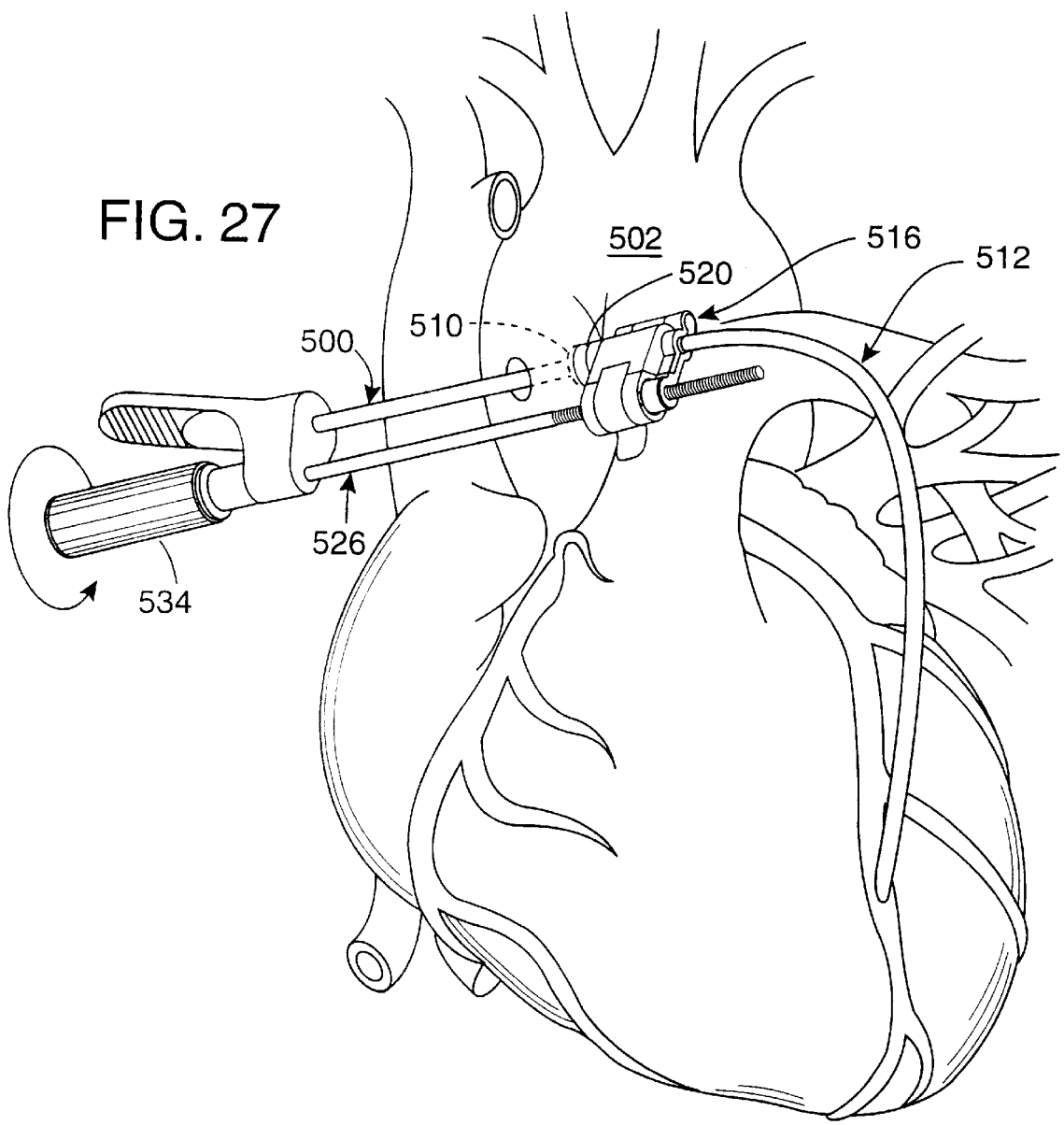
Figure 28:
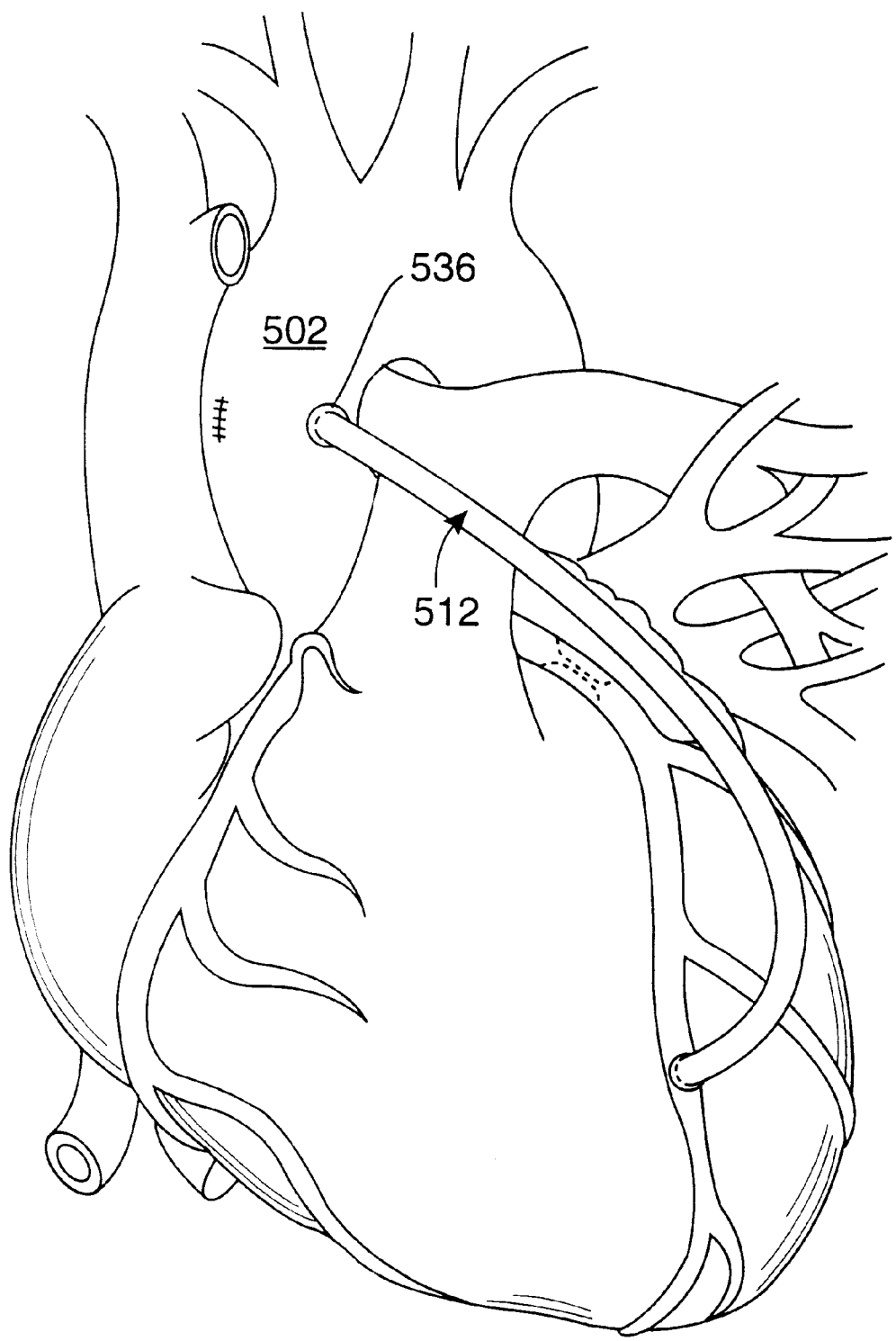

Moving now to FIG. 27, there is shown driver handle 534 rotated in a clockwise direction, bringing together anvil 510 and cylindrical sleeve 520. The clockwise rotation is continued until the aorta wail 502 is engaged with the distal end 518 of vein 512 upon which the staple driver pins (not visible) are fully engaged within each of the corresponding staple shafts (not visible), driving the staples (not visible) through the engaged tissue to create anastomotic bond 536 between aorta 502 and vein 512 (See FIG. 28).

Figure 36:
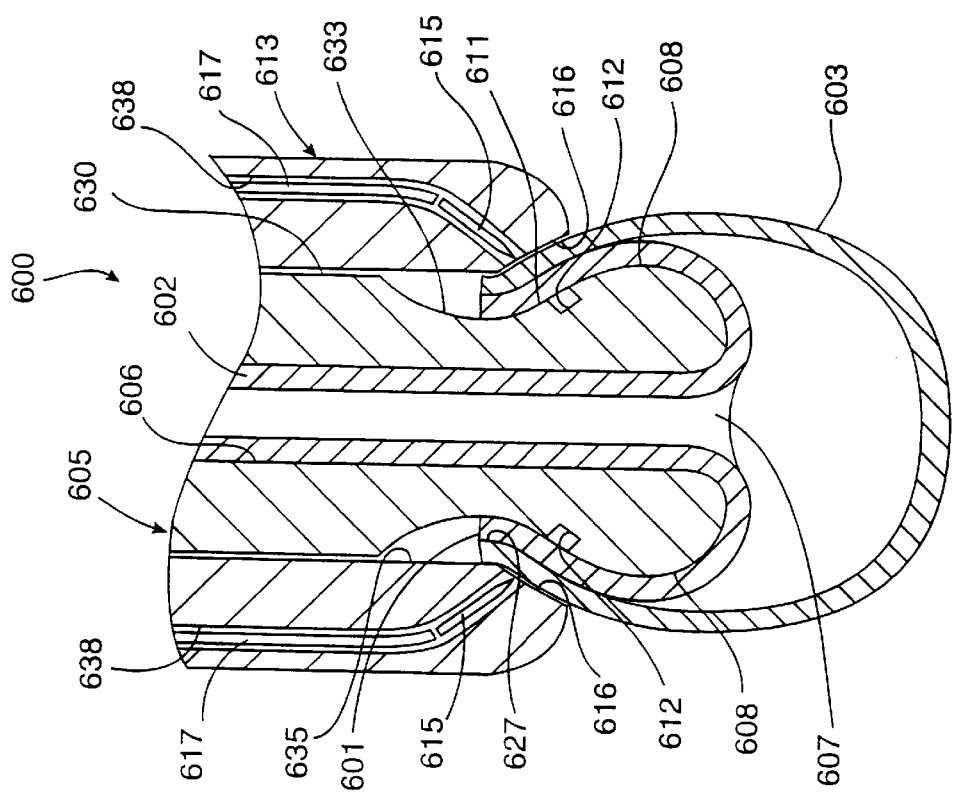
FIG. 36 is an enlarged, fragmentary side elevation view, in cross-section, of the anastomosis device of FIG. 29 illustrating a compression device in a compressed condition.
Figure 37:
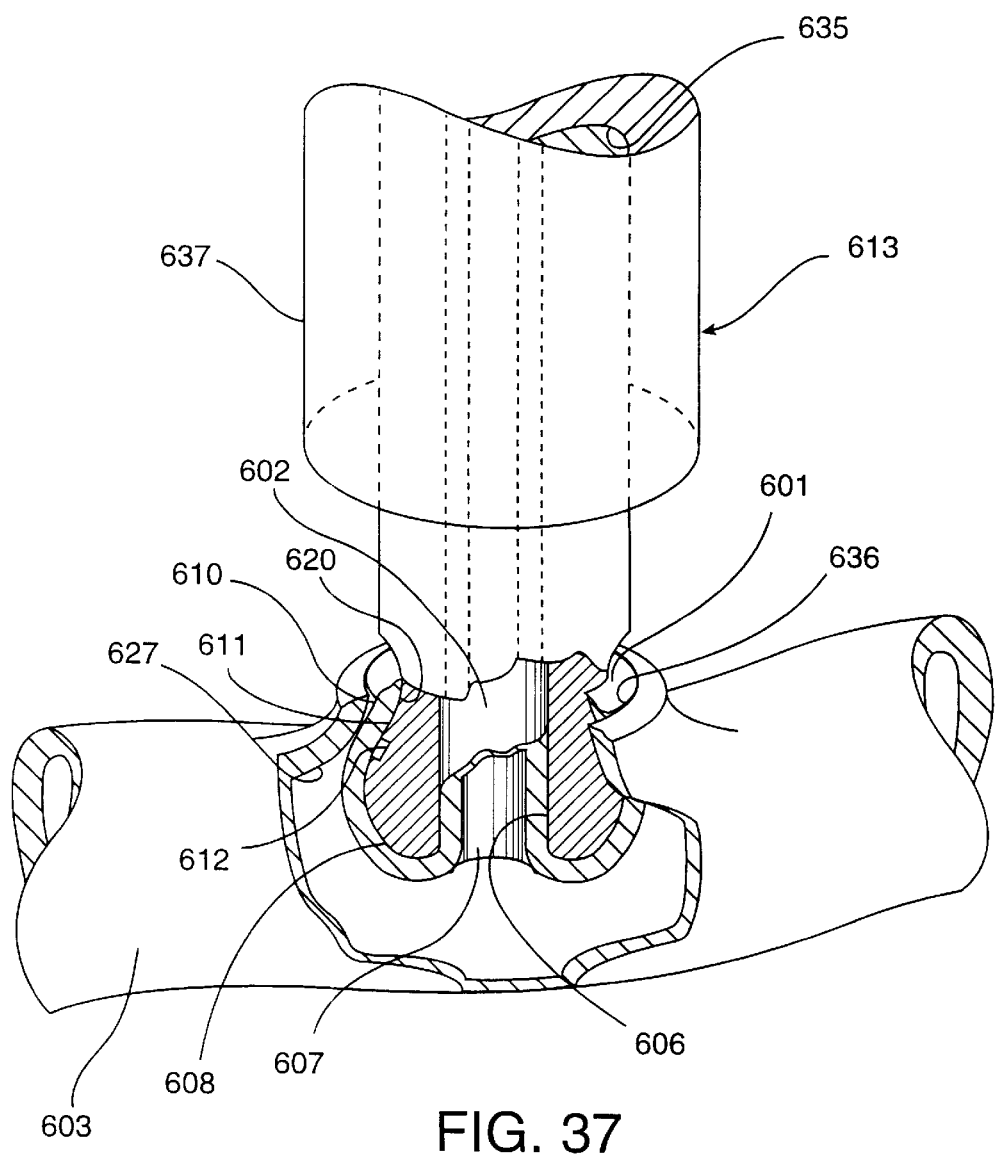
FIG. 37 is an enlarged, fragmentary, top perspective view, partially cut-away, of the eversion mandrel of the anastomosis device of FIG. 29 positioned in a surgically formed opening in a luminal structure.
Figure 39:
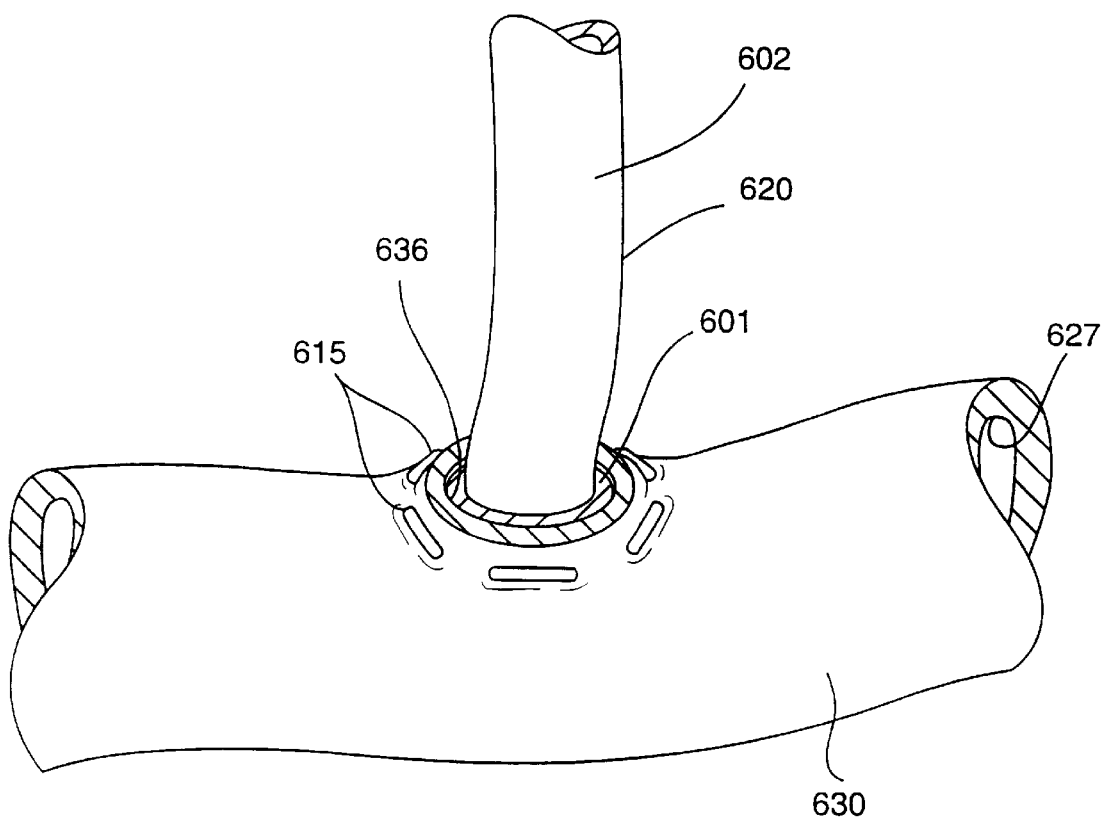
FIG. 39 is an enlarged, fragmentary top perspective view of a tubular tissue structure grafted to the luminal structure employing the anastomosis device of FIG. 29.

In another aspect of the present invention, as viewed in FIGS. 29–37 with like numbers referencing like elements, an end-to-side surgical anastomosis apparatus, generally designated 600, and procedure for end-to-side anastomosis is provided for stapling an end 601 of a tubular tissue structure 602 to a side portion of a luminal structure 603 (FIG. 37). The anastomosis apparatus 600 includes an elongated tubular housing or eversion mandrel, generally designated 605, defining a central bore 606 extending longitudinally therethrough and terminating at a bore opening 607 at a distal end of the tubular housing. The central bore 606 includes a transverse cross-sectional dimension sufficiently sized and configured for receipt of the tissue structure 602 therein in a manner positioning the end of the tissue structure through the bore opening. The elongated tubular housing further includes an eversion support surface, generally designated 608, extending circumferentially about the bore opening 607 adjacent the distal end. This surface 608 is configured to retain and support an everted end 601 of the received tissue structure 602 in a position facing an intimal surface 610 of the tissue structure 602 in a radially outward direction. The anastomosis apparatus 600 further includes an anvil 611 having a fastener engaging surface 612 positioned in the eversion support surface, and a plurality of fasteners 615 (FIG. 30) coupled to the apparatus. A compression device, generally designated 613, is included having a shoulder portion 616 formed for selectively compressing the everted end 601 of the tissue structure 602 and a surface of the luminal structure 603 together against the fastener engaging surface 612. Preferably, at least one driver pin 617 is provided moveable relative to the compression device 613 for ejecting the plurality of deformable fasteners from the compression device, through the everted end of the tubular tissue structure and the luminal structure to engage the fastener engaging surface. This engagement deforms the fasteners and creates an anastomotic bond between the tubular tissue structure and the luminal structure.

While this configuration still requires the end of the grafted tubular tissue structure 602 to be everted over the distal end of the mandrel (i.e., the everted end) for positioning against the eversion support surface 608, the fastener engaging surface 612 of the anvil 61 1 is positioned on the eversion support surface 608 adjacent the bore opening 607. Hence, unlike the previous embodiments of the present invention, the everted end of the tubular tissue structure is everted over the anvil structure as well.

Figure 30:
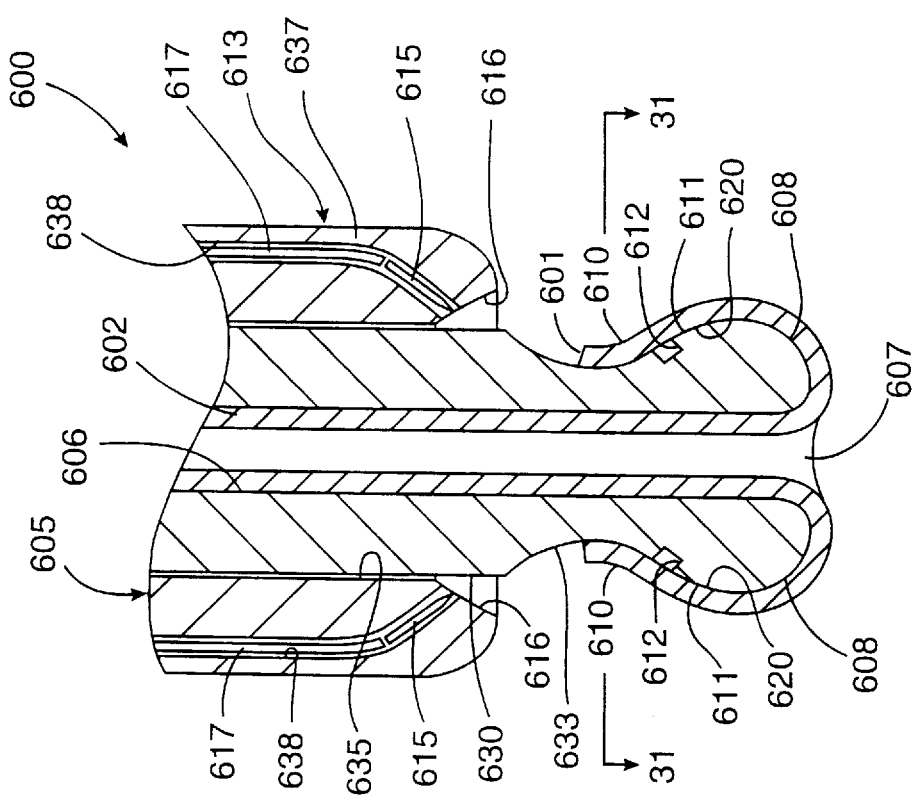
FIG. 30 is an enlarged, fragmentary side elevation view, in cross-section, of the anastomosis device of FIG. 29 illustrating a distal end of the tubular tissue structure everted over a distal end of the eversion mandrel.
Figure 31:
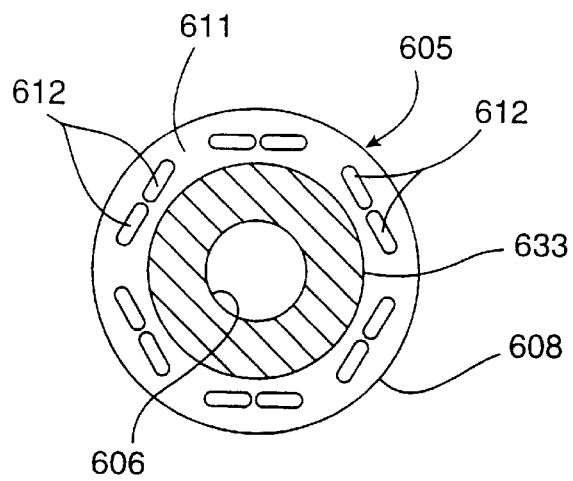
FIG. 31 is a top plan view of the anastomosis device of FIG. 29 taken substantially along the plane of the line 31—31 in FIG. 30.

In this embodiment, the deformable fasteners 615 are preferably provided by conventional staples formed to pierce through the tissues to be anastomotized. Other deformable fasteners, however, could be employed such as deformable clips or the like. Accordingly, fastener engaging surface 612 is preferably provided by a plurality of pairs of fastener deforming recesses circumferentially spaced about bore opening 607 (FIGS. 30 and 31). Each deforming recess 612 is similar in function and shape as the fastener deforming recesses in the embodiment illustrated in FIG. 4. Further, the fastener engaging surface 612 (i.e., deforming recesses) of this embodiment is preferably integrally formed and recessed in the eversion support surface 608 of the mandrel 605. When the everted end 601 of the tubular tissue structure 602 is resiliently everted over the mandrel distal end and into supportive contact with the eversion support surface 608, accordingly, the fastener engaging surface 612 is positioned underneath the adventitial surface 620 of the everted tissue.

The everted end 601 is maintained and retained in the everted condition against the eversion support surface 608 by the resiliency of the tubular tissue structure. This is performed by sufficiently sizing the transverse cross-sectional dimension of the eversion support surface, relative the transverse cross-sectional dimension of the tubular tissue structure, for resilient cooperation therebetween. It is important, however, that the transverse cross-sectional dimension of the eversion support surface be sufficiently small to ensure that the structural integrity of the everted end will not be compromised when everted over the mandrel distal end.

In addition, a securing device may be included to maintain the everted end of the tubular tissue everted over the end of the eversion mandrel. For example, a plurality of tines or the like may protrude outwardly from the eversion support surface which penetrate and retain the everted tissue over the distal end of the mandrel in the everted condition. Furthermore, a suture may be provided to removably secure or tie the everted end to the eversion support surface.

To assure that the fastener engaging surface 612 is positioned for engagement with the fasteners or staples 615 ejected from the compression device 613, the recesses 612 are situated at a portion of the eversion support surface which faces in the direction of the staple shoulder portion 616. This alignment enables engagement and deformation of a respective staple 615 with the respective deforming recess upon ejection thereof from compression device 613. In the bell-shaped eversion support surface 608 illustrated in FIG. 32 (to be discussed below), the fastener engaging surface 612 is situated along a lower annular rim portion 621 of the support surface 608.

Figure 33:
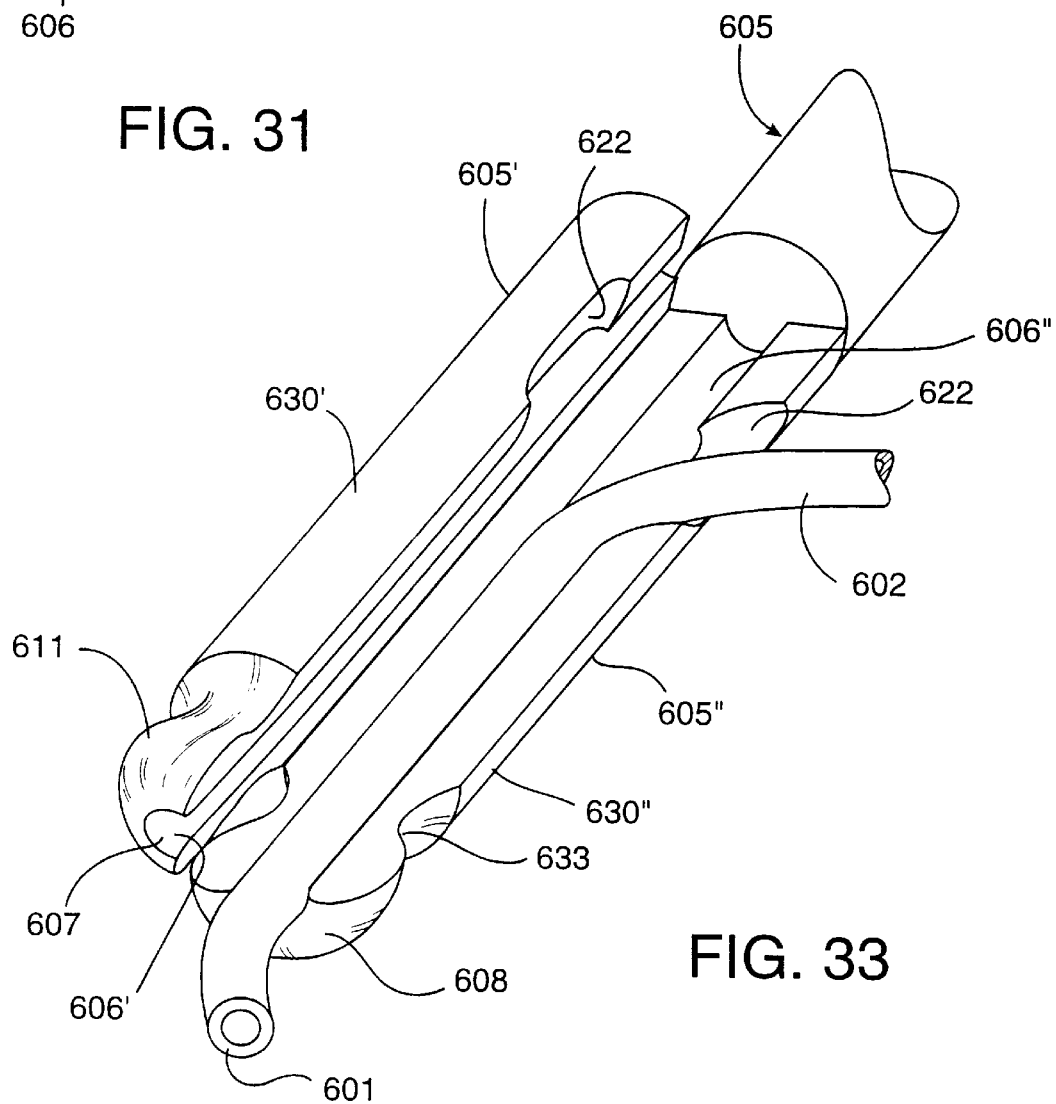
FIG. 33 is a fragmentary, top perspective view of the eversion mandrel of anastomosis device of FIG. 29 in an opened condition.

Referring now to FIG. 33, it is shown that the central bore is generally linear extending longitudinally through mandrel 605 parallel to the longitudinal axis thereof. Bore 606 is sufficiently sized and configured for receipt of the tubular tissue structure 602 therein without substantially deforming or damaging the tissue structure during loading of the tissue therein, and is of a length sufficient to accommodate the free graft intended for use. Further, the central bore terminates at the central bore opening 607 at the distal end of the eversion mandrel 605. Before eversion of the everted end of the tubular tissue structure over the distal end of the eversion mandrel or tubular housing 605, the tubular tissue structure must be properly positioned in the central bore 606 where the distal end of the tubular tissue structure protrudes past the distal end of the eversion mandrel. This extension beyond the mandrel or tubular housing distal end must be an amount sufficient to enable the eversion of the tubular tissue structure 602 over the fastener engaging surface 612 of the anvil 611.

To anastomotize attached graft tubular tissue structures having only one free unattached end, such as an Internal Mammary Artery (IMA) graft or the like, a side port 622 is provided at a side wall portion of the eversion mandrel 605 which communicates with the central bore 606. This port enables the attached graft tissue structure 602 to enter the central bore from the side of the eversion mandrel without requiring that the graft be free at both ends. FIG. 33 best illustrates that the attached graft tissue structure 602 enter side port 622, extend through central bore 606 and exits bore opening 607 before being everted over the mandrel distal end for resilient support by eversion support surface 608. The side port 622 is preferably circular or oval shaped in cross-sectional dimension, and curving inwardly toward the central bore. The port, however, may be virtually any other shape which is sufficiently sized for the passage of the tubular tissue structure therethrough. It will be understood that both the central bore and the side port should be free of any sharp edges or the like which are likely to cause any cutting, nicking or any inadvertent damage to the loaded tubular tissue structure during operation of the anastomosis apparatus.

Figure 29:
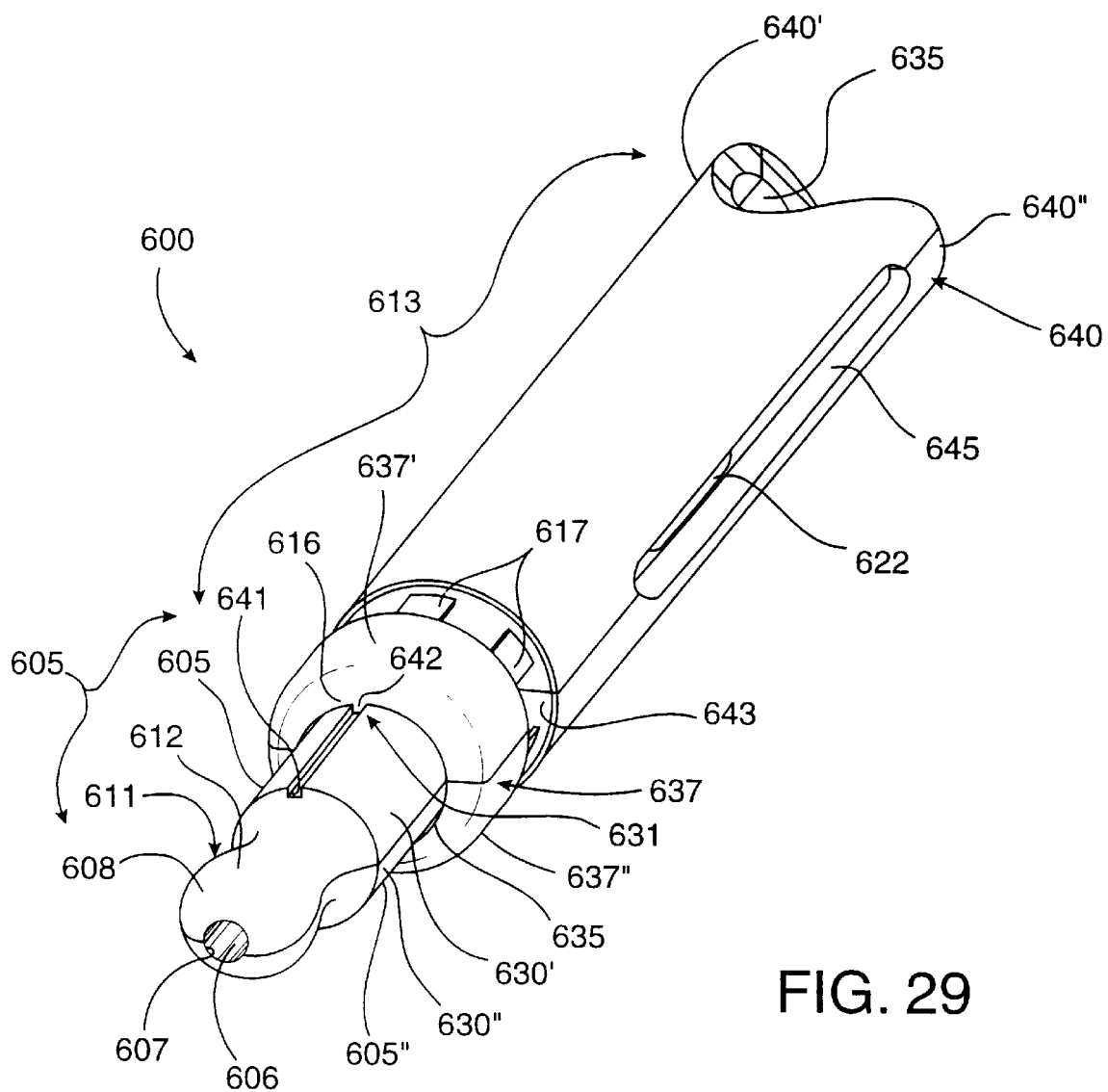
FIG. 29 is a fragmentary, top perspective view of an alternative embodiment anastomosis device constructed in accordance with the present invention.

To facilitate the delicate placement of the tubular tissue structure 602 in the elongated central bore 606, the mandrel 605 is formed to move to an opened condition for increased access and exposure of all or a substantial portion of the central bore 606. This is accomplished by providing a clam shell type design for the lower end portion of the eversion mandrel 605, similar in concept to the embodiment set forth in FIG. 23. In the preferred embodiment, the lower end portion of mandrel 605 is divided into a first half 605' and a second half 605" which are pivotally coupled together for pivotal movement between an opened condition (FIG. 33) and a closed condition (FIG. 29). In the open condition, the mandrel or tubular housing 605 is pivotally opened to expose, substantially longitudinally, the central bore 606 so that the tubular tissue structure 602 may be easily positioned therein. In the closed condition, the lower end portion of the eversion mandrel closes over the loaded tubular tissue structure to enclose the same in the central bore 606.

The first and second halves 605', 605" are preferably mirror-images of one another and are semi-cylindrical in shape. Each eversion mandrel half further defines one half of the central bore 606 (i.e., a semi-cylindrical first and second bore half 606', 606") which collectively cooperate to form the bore when the mandrel is moved to the closed condition. The relative pivotal movement is provided by a longitudinally extending hinge 623 (FIGS. 33 and 34) pivotally coupling the first half 605' to the second half 605". Preferably, hinge 623 includes an elongated pin or gudgeon member 625 extending longitudinally along an edge of one of the mandrel halves generally parallel to the central bore, while the other mandrel half defines an elongated socket 626 extending longitudinally along an opposing edge of the same. Each of the gudgeon member 625 and mating socket 626 are integrally formed with the respective mandrel half, and each is sized and configured relative one another for mating pivotal coupling therebetween. Hence, once slidably coupled, as shown in FIG. 34, the opposing mandrel halves 605', 605" matingly engage and cooperatively pivot between the opened condition (FIG. 33) and the closed condition (FIG. 29).

In accordance with the present invention and as will be described in greater detail below, the compression device 613 is coupled to eversion mandrel 605 for sliding movement longitudinally along the mandrel between a released condition (FIG. 33) and a compressed condition (FIG. 36). Briefly,. in the released condition, the eversion mandrel is permitted to move between the closed condition and the opened condition, enabling loading of the tissue structure in the central bore. In the compressed condition, the staple apparatus 600 selectively compresses an intimal surface 610 of the everted end 601 of the tissue structure 602 to an intimal surface 627 of the luminal structure 603.

To prevent interference with the sliding movement of the compression device 613 by the hinge 623, the hinge is preferably recessed from the exterior surface 630 of the mandrel 605. As best viewed in FIG. 34, both the gudgeon member 625 and the socket 626 are positioned along opposing edge walls 628', 628" of the respective first and second mandrel halve 605', 605" between the respective exterior surface 630', 630" and the central bore half 606', 606" thereof. Accordingly, the hinge 623 does not protrude into the path of the compression device 613 to impede movement as the assembly slides over the hinge 623 between the released and compressed conditions.

It will be appreciated that a variety of other hinges or coupling devices could be employed without departing from the true spirit and nature of the present invention. Moreover, a hinge could be provided which does protrude into the path of sliding movement of the compression device (not shown) which would normally impede the movement to the compressed condition. In this arrangement, the protruding hinge may function as both a hinge and as a key member or the like for an alignment mechanism 631 (to be discussed later) to align movement of the compression device 613 relative the eversion mandrel 605.

To enable pivotal movement of the mandrel halves 605', 605" between the closed and the opened conditions, at least one of, and preferably both, the opposing edge walls 628', 628" includes a tapered wall portion 632', 632" which tapers away from the opposing edge wall. The collective angle of tapered wall portions 632', 632" will determine the relative pivotal movement between the mandrel halves 605', 605" about the hinge member 623. In the preferred embodiment, these opposing tapered wall portions 632', 632" are adapted to limit the pivotal movement of the mating halves 605', 605" in the opened condition (phantom lines in FIG. 34) between about 45° to about 120°. This opening angle need only be suufficiently large to enable positioning of the attached or free graft into the exposed central bore 606. Since the diameter of these grafts are relatively small, the opening angle need not be very large.

Once the tubular tissue structure is properly positioned in the one side of the semi-cylindrical bore portion, while the eversion mandrel is in the opened condition (FIG. 33), the mandrel halves 605', 605" are moved to the closed condition (FIG. 29) enclosing the tubular tissue in the central bore. By positioning the distal end of the tubular tissue structure 602 beyond the distal end of the eversion mandrel (FIG. 3), the everted end 601 of the tissue structure can be everted back over the distal end of the mandrel either through manually rolling the tissue onto the generally spherical shaped eversion support surface or through the assistance of medical instruments.

As best shown in FIG. 30, it is imperative that the everted tissue extend over the anvil 611 so that the fastener engaging surface 612 is positioned beneath the adventitial surface 620 of the everted tissue structure. Preferably, the everted end is of a length sufficient to enable the distal end to terminate at a neck portion 633 of the eversion support surface 608 which is positioned rearward of the fastener engaging surface 612. By tapering the neck portion 633 inwardly from the eversion mandrel exterior surface 630, contact of the tissue structure distal end with the sliding compression device 613 will be prevented when the compression device is moved to the compressed condition.

When the eversion mandrel is moved to the closed condition, the transverse cross-sectional dimension of the central passage 635 of the compression device 613 is sized and dimensioned for longitudinal sliding receipt of mandrel therein. As above mentioned, the lower end portion of the eversion mandrel is slidably received in the central passage 635 of the compression device 613 between a released condition and a compressed condition. In the released condition (FIG. 33), the compression device 613 is moved to a position, relative the eversion mandrel, which will not impede the movement of the mandrel half 605', 605" between the opened and closed conditions. Accordingly, in the released condition, the mandrel half portions can be pivotally moved to the opened condition so that the attached or unattached grafted tubular tissue structure can be either loaded or removed from the exposed central bore 606.

In contrast, in the compressed condition, the compression device 613 is moved slidably and longitudinally along the exterior surface of eversion mandrel 605 toward the eversion support surface 608 until the tissue structures to be anastomotized are compressed between the shoulder portion 616 of the compression device 613 and no the eversion support surface 608 of the eversion mandrel. As shown in FIG. 37, the everted end of the tissue structure 602 mounted to the distal end of eversion mandrel 605 is moved forwardly through the surgically formed opening 636 in the side of the luminal structure 603 until the distal end of the mandrel is positioned in the luminal structure. It is noted that the surgically formed opening 636 in the resilient luminal structure is preferably smaller in cross sectional dimension than that of the eversion support surface 608. Once the distal end of the mandrel 605 and the everted tissue structure 601 mounted thereon are positioned in the luminal structure 603, the two are retracted rearwardly as a unit until the intimal surface 610 of the everted tissue structure 602 contacts the intimal surface 627 of the luminal structure 603 adjacent the surgically formed opening 636. Due to the resilient nature of the tissue, circumferential contact between the adjacent tissue structures is facilitated. Hence, upon proper positioning of the everted end of the tubular tissue structure and the lower end of the eversion mandrel through the surgically formed opening 636 (FIGS. 36 and 37), the intimal surface 610 of the everted tubular tissue structure 602 circumferentially contacts the intimal surface 627 of the luminal structure 603 adjacent the fastener engaging surface 612. The compression device 613 can then be moved to the compressed condition, compressing the everted end of the tissue structure and the tissue of the luminal structure 603 between the shoulder portion 616 of the compression device 613 and the eversion support surface 608 of the eversion mandrel 605. Subsequently, the stapler compression device can be prepared for ejecting or firing the staples therefrom to form an intimal-to-intimal surface anastomotic bond.

Accordingly, using the method and anastomosis apparatus of the present invention, the end-to-side anastomotized tissues juncture will be free of any portion of the fastener protruding into the lumen of either the graft vessel or target vessel to interfere with blood flow (FIG. 38) This arrange will reduce the risk of thrombus formation.

Employing a concept similar to the previous embodiments, compression device 613 includes a disposable circular staple cartridge 637 encasing a circular array of staple delivery shafts 638. The shafts 638 may be arranged in a plurality of concentric arrays or rows of staple shafts to best perform these anastomotic procedures. Although the present invention is primarily described and depicted as forming staple bonds that are circular and as having component circumferences that are circular, other embodiments are realized for forming staple bonds having elliptical, tear drop, generally oval or other non-circular shapes. Accordingly, the anvil and associated array of deforming recesses 612 (i.e., the fastener engaging surface 612), and the staple cartridge 637 and associated staple shaft array of these alternative stapler embodiments have circumferences in the shape of the desired staple bond.

Referring now to FIGS. 29 and 35, compression device 613 is shown including a tubular drive housing 640 operatively coupled to staple cartridge 637 for driving staples from the cartridge 637 into engagement with the fastener engaging surface 612 positioned on eversion mandrel 605. The drive housing 640 and the staple cartridge 637 each define a segment of central passage 635 which as mentioned is formed for sliding receipt of the eversion mandrel therein.

To promote alignment between the array of staple shafts 638 and the corresponding staples 615 therein, and the respective fastener deforming recesses 612, an alignment mechanism 631 may be provided operatively positioned between the eversion mandrel and the compression device 613 and the drive housing 640. Preferably, as best viewed in FIG. 29, the alignment mechanism 631 is provided by a key member 641 protruding into the central passage 635 from an interior wall of the compression device (,i.e. either the staple cartridge 637, the driver housing 640, or both), and a longitudinally extending groove 642 provided in the exterior surface of the eversion mandrel 605. The key member 641 is formed and dimensioned for sliding receipt in the alignment groove 642 for aligned movement of the staple cartridge 637 relative the eversion mandrel 605. It will be understood that the eversion mandrel could include a key member while the compression device defines the groove, or that any other alignment mechanism could be employed to align the two components without departing from the true spirit and nature of the present invention. For example, as set forth above, the key member could be provided by a protruding hinge member of the eversion mandrel protruding into the central passage of the compression device.

Mounted to and protruding perpendicularly outward from the face 643 of drive housing 640 is a plurality staple driver pins 617 aligned in an array (circular in FIGS. 29 and 35) conforming to the delivery shaft pattern of the staple cartridge 637. Staple cartridge 637 encases, from end to end, a cylindrical array of hollow staple delivery shafts 638 each of which hold a preloaded staple 615. All shafts 638 are identical and each has height and width dimensions such that a corresponding staple driver pin 617 is slidable therein. In the configuration of the FIG. 30, due to the position and orientation of the deforming recesses 612 positioned on the eversion support surface 608, the staples 615 are preferably ejected from the cartridge housing at about a 30° to about 60° angle, and most preferably about 45° angle, from the vertical. This angle assures that the staples penetrate the tubular tissue and the luminal tissue generally perpendicular thereto to form a proper anastomotic bond.

Each staple shaft 638, thus, will curve inwardly from a direction parallel to the longitudinal axis of the central passage 635 to the desired angle toward the axis. Hence, to slidable accommodate such a curvature, the driver pins 617 will have to be resiliently flexible in nature. For example, the driver pins may be composed of stainless steel, plastic or the like.

The staple cartridge 637 is preferably provided by a disposable cartridge which is disposed of and replaced after one anastomotic stapling. This assures that the staple shafts and central passages are clean, sterile and clear of blockage during operation. In another embodiment, a slidable sleeve (not shown) may be provided around the driver pin array to prevent blood and tissue from getting caught therein.

Again, it is imperative not to injure the living tissue being stapled by overcompressing it between the fastener engaging surface 612 of anvil 611 and the shoulder portion 616 of the staple cartridge 637, or by a staple bond that is exceedingly tight. Accordingly, overcompression of the tissue is again prevented in this embodiment of the present invention by limiting the length of driver pins 617.

Similar to the embodiment of FIG. 7, a threaded proximal end of eversion mandrel 605 may be provided which extends beyond the length of the delivery housing 640 (not shown) to threadedly engage with a nut. This nut may include an internally threaded throughbore extending the full length of cylindrical nut which allows the threaded end to exit therethrough.

Moreover, an off-set assembly may be employed to control the movement of the compression device 613 between the compressed condition and the released condition. Briefly, in this configuration (not shown; however similar to but in the reverse direction of the off-set mechanism employed in the embodiment of FIGS. 17 and 18), eversion mandrel 605 (handle 402) is slidably received in the central passage 635 of compression device 613 (staple cartridge 418). An off-set housing portion (cylindrical casing 442) of compression device 613 is movably coupled to and cooperating with an off-set driver rod (driver rod 406), axially off-set from eversion mandrel 605, to drive the movement of the compression device between the released and the compressed conditions. Similar to the off-set mechanism of FIGS. 17 and 18, the driving force may be provided by a threaded end (driver rod end 412) or a threaded handle portion (handle 402 at bore 416) whereby the off-set housing portion of compression device 613 would be rigidly coupled to the off-set driver rod (driver rod 406).

Both the staple cartridge 637 and the delivery housing 640 may incorporate a clam-shell design in which each housing provides a semi-cylindrical half portion (637', 637" for cartridge 637, and 640', 640" for delivery housing 640). Each half portion of the compression device is preferably hingedly mounted together, through independent hinge members, at a respective edge portion, similar to the eversion mandrel. The half portions, however, may be simply snapfit together as well. In either configuration, the half portions will be independently, or cooperatively, movable between an opened position (not shown) and a closed position (FIG. 35). In the opened condition, the respective half portions are cooperatively pivoted along a pivotal axis of the hinge members, parallel to the longitudinal axis of the central passage. This pivotal movement will pivot the corresponding half portions, and away from one another to expose the central bore 606. The relative pivotal movement of the housing half portions is by an amount sufficient to enable receipt of the eversion mandrel 605 in the central passage 635 when the eversion mandrel is in the closed condition.

In the closed position of the compression device, as illustrated in FIG. 35, the housing half portions (637', 637" for cartridge housing 637, and 640', 640" for delivery housing 640) are enclosed about the loaded eversion mandrel. This arrangement enables sliding receipt of the eversion mandrel 605 from the released condition to the compressed condition before firing of the staples from the staple shafts.

To accommodate attached grafts, the delivery housing includes an elongated delivery slot 645 in alignment with side port 622 of the eversion mandrel for receipt of the attached end of the graft therethrough. As best viewed in FIG. 35, slot 645 is sufficiently sized and configured to enable movement of the delivery housing between the released and the compressed conditions. Accordingly, slot 645 is relatively linear and generally extends in a direction parallel to the mandrel longitudinal axis from one end of the proximal end to the distal end of the delivery housing.

Figure 38:
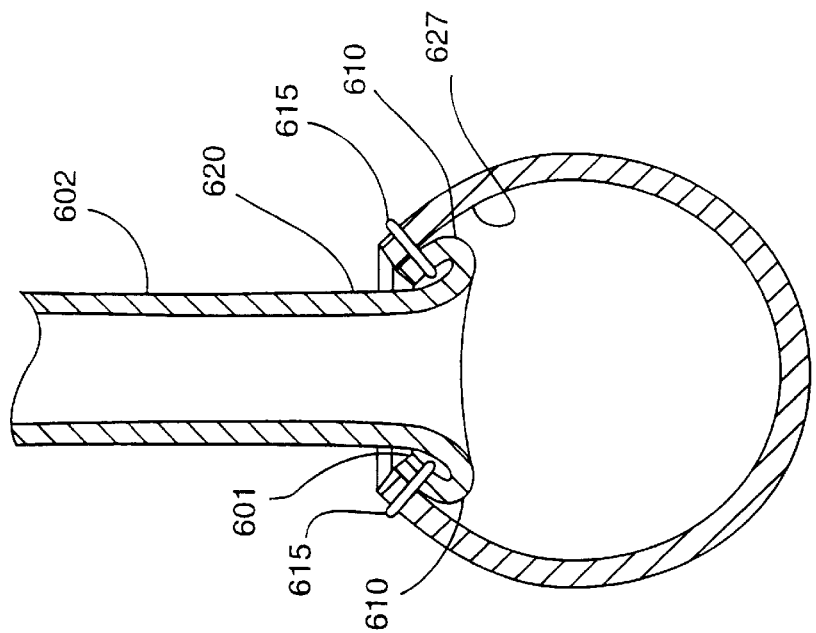
FIG. 38 is an enlarged, fragmentary side elevation view, in cross-section, of the tubular tissue structure crafted to the luminal structure employing the anastomosis device of FIG. 29.

FIGS. 36–38 illustrate the mechanical interaction between the staple driver pins 617, staple cartridge 637 and eversion mandrel anvil 611 upon operational engagement therebetween. In accordance with the present invention, after the graft has been loaded into the central bore of the eversion mandrel, and the everted end thereof has been everted over the distal end of the mandrel, the compression device can be moved to the closed position. In this configuration, before the assembly is moved to the compressed condition, the array of staple delivery pins 617 mounted on face 643 of delivery housing 640 are slidably engaged within the array of staple delivery shafts 638 of staple cartridge 637. The array of staples 615 is projected from staple cartridge 637 and through the tissues to be stapled (not shown). Similar to FIG. 9, once the driver pins 617 contact the respective staples 615, the staples are ejected or fired from the staple shafts and driven through the tubular tissue structure and the luminal tissue adjacent the surgically formed opening until the staples contact and are deformed by the deforming recesses 612 to form an intimal-to-intimal anastomotic bond.

Moreover, a spring-loaded engagement between the compression device 613 and the eversion mandrel 605 enabling independent compression of the tissues, and independent stapling thereof is also preferably applicable for this embodiment of the present invention. Such a stapler device is illustrated in commonly owned and co-pending U.S. patent application Ser. No. 08/597,691, filed Feb. 6, 1996, hereby incorporated by reference in its entirety. This arrangement enables independent compression of the tissues between the compression device shoulder portion 616 and the anvil 611 of the eversion mandrel 605 before the firing step commences, firing or ejecting the staples through the tissues. This assures that the overcompression of the tissues does not occur during the firing step.

Figure 32:
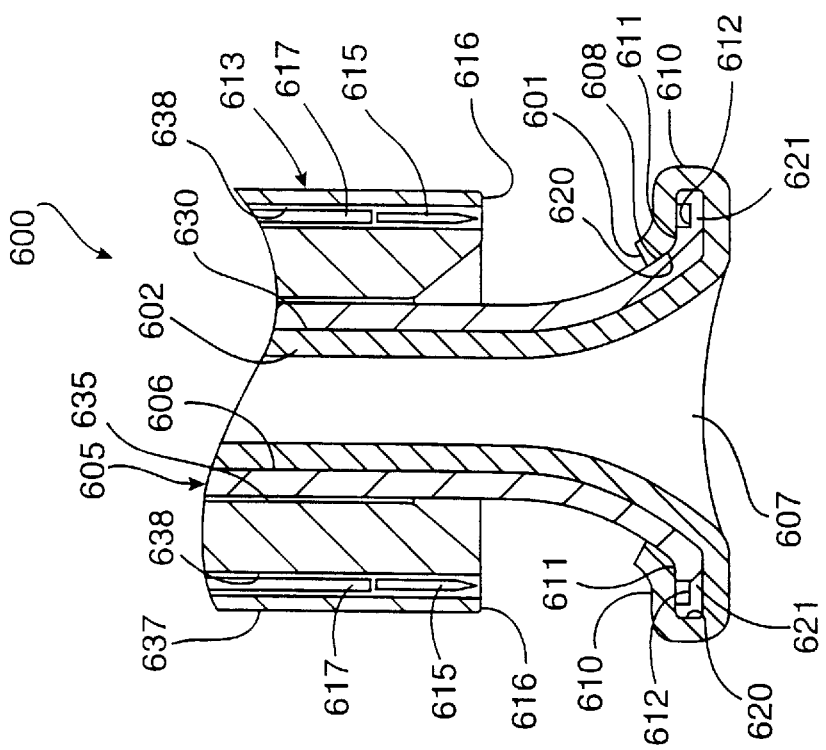
FIG. 32 is a fragmentary side elevation view, in cross-section, of an alternative embodiment bell-shaped distal end of the eversion mandrel of FIG. 31 having the tubular tissue structure everted over a distal end of the bell-shaped eversion mandrel.

As above-mentioned and as shown in FIG. 32 eversion support surface 608 may be bell-shaped having a distal end of the eversion mandrel 605 which tapers outwardly. In this embodiment, the fastener engaging surface 612 (i.e., the deforming recesses) is positioned circularly about bore opening 607 on lower annular rim portion 621. The annular rim portion 621 is oriented generally perpendicular to the direction of travel of the compression device 613 so that the deforming recesses face the corresponding staple shafts 638 perpendicularly without requiring any curvature of the shafts.

Similar to the previous embodiment, the everted end of the tubular tissue structure is everted over the distal end of the eversion mandrel 605 so that the adventitial surface 620 of the tissue structure is resiliently supported against the fastener engaging surface. It will further be appreciated that in either the generally spherically shaped eversion support surface or the bell-shaped eversion support surface, the transverse cross-sectional dimension of the eversion support surface 608 is larger than the transverse cross-sectional dimension of the central passage 635. This arrangement prevents the compression device from slipping past the end of the eversion support surface when the mandrel is operatively positioned in the compressed condition (FIGS. 32 and 36).

It will be understood that the foregoing is only illustrative of the principles of the present invention, and that various modifications can be made by those skilled in the art without departing from the scope and spirit of the invention. For example, the particular stapler structural configurations shown are not critical and other configurations can be used if desired. One possible alternative for the configuration illustrated in FIG. 17 is to have a vessel rod that is retractable (e.g., by means of a telescoping rod). In addition, the vessel rod of this alternative embodiment can be curved to facilitate the anastomotic procedure if necessary. Also, the structure and method of the present invention can be employed thoracoscopically.

What is claimed is:

1. A method of end-to-side surgical anastomosis between a tubular tissue structure, having at least one end, and a luminal structure, such as a vascular lumen or another tubular tissue structure, comprising the steps of:

everting an end of the tubular tissue structure to face an intimal surface thereof in an outward direction;

contacting the intimal surface of the everted end with a surface of the luminal structure adjacent a surgically formed opening therein; and simultaneously applying a plurality of staples to said tubular tissue structure and said luminal structure to form an anastomotic bond between the intimal surface of the tubular tissue structure and the surface of the luminal structure.

2. The surgical anastomosis method of claim 1 wherein the surface of the luminal structure is an adventitial surface thereof.

3. The surgical anastomosis method of claim 1 wherein, said plurality of fasteners are applied to the tubular tissue structure and the luminal structure in a non-circular arrangement.

4. The surgical anastomosis method of claim 1 wherein, said everted end is maintained in a non-circular shape during said step of applying.

5. The surgical anastomosis method of claim 1 wherein, the non-circular shape is generally tear-drop shaped.

* * * * *